(12) United States Patent
Mesilaty-Gross et al.

(10) Patent No.: US 8,518,656 B2
(45) Date of Patent: Aug. 27, 2013

(54) PROCOLLAGEN C-PROTEINASE ENHANCER (PCPE) BIOMARKER FOR BONE FORMATION

(75) Inventors: Shlomit Mesilaty-Gross, Kochav Yair (IL); Yair Anikster, Jerusalem (IL); Ido Wolf, Or-Yehuda (IL); Efrat Kessler, Tel-Aviv (IL)

(73) Assignees: Ramot Tel-Aviv University Ltd., Tel-Aviv (IL); Tel Hashomer Medical Research Infrastructure and Services Ltd., Ramat-Gan (IL)

( * ) Notice: Subject to any disclaimer, the term of this patent is extended or adjusted under 35 U.S.C. 154(b) by 143 days.

(21) Appl. No.: 13/310,205

(22) Filed: Dec. 2, 2011

(65) Prior Publication Data

US 2012/0270246 A1 Oct. 25, 2012

Related U.S. Application Data

(63) Continuation-in-part of application No. 12/936,035, filed as application No. PCT/IB2009/051376 on Apr. 1, 2009.

(60) Provisional application No. 61/064,901, filed on Apr. 2, 2008.

(51) Int. Cl.
*G01N 31/00* (2006.01)
*G01N 33/53* (2006.01)

(52) U.S. Cl.
USPC ........... 435/7.21; 435/7.1; 436/501; 436/518; 422/430; 424/9.1

(58) Field of Classification Search
None
See application file for complete search history.

(56) References Cited

U.S. PATENT DOCUMENTS

| | | | |
|---|---|---|---|
| 4,857,456 A | 8/1989 | Urist | |
| 6,037,139 A | 3/2000 | Greenspan et al. | |
| 6,803,453 B1 | 10/2004 | Brunkow et al. | |
| 2003/0224501 A1 | 12/2003 | Young et al. | |
| 2011/0143371 A1 | 6/2011 | Mesilaty-Gross et al. | |

FOREIGN PATENT DOCUMENTS

WO 02068962 A2 9/2002

OTHER PUBLICATIONS

Yang L, Grey V. Pediatric reference intervals for bone markers. Clin Biochem. 2006 39(6):561-8.
Seibel MJ. Biochemical markers of bone turnover: part I: biochemistry and variability. Clin Biochem Rev. 2005 26 (4):97-122.
Gelse K, Poschl E, Aigner T. Collagens—structure, function, and biosynthesis. Adv Drug Deily Rev. 2003 55 (12):1531-46.
Voorzanger-Rousselot N, Garnero P. Biochemical markers in oncology. Part I: molecular basis. Part II: clinical uses. Cancer Treat Rev. 2007 33: 230-283.
Barry M. Steiglitz et al."Procollagen C Proteinase Enhancer 1 Genes Are Important Determinants of the Mechanical Properties and Geometry of Bone and the Ultrastructure of Connective Tissues" Molecular and cellular biology. Jun. 2006, p. 238-249.
Ogata et al. "Type I procollagen C-proteinase enhancer protein (PCPE) is expressed in cirrhotic but not in normal rat liver." Hepatology 26: 611-617. (1997).
Lovorka et al. "Detection of bone and cartilage-related proteins in plasma of patients with a bone fracture using liquid chromatography-mass spectrometry." International Orthopaedics 31(6): 743-751. (2007).
Kessler-Icekson et al. "Expression of procollagen Cproteinase enhancer-1 in the remodeling rat heart is stimulated by aldosterone." Int J Biochem Cell Biol. 38: 358-365. (2006).
Kobayashi et al. "Secreted Frizzled-related protein 2 is a procollagen C proteinase enhancer with a role in fibrosis associated with myocardial infarction." Nature Cell Biology 11: 46-55. (2008).
Shalitin et al. "Expression of procollagen C-proteinase enhancer in cultured rat heart fibroblasts: Evidence for coregulation with type I collagen." J Cell Biochem. 90: 397-407. (2003).
De Jong et al. "Biomarkers of myocardial fibrosis." J Cardiovasc Pharmacol. 57:373-375. (2011).
Gressner et al. "Biomarkers of liver fibrosis: Clinical translation of molecular pathogenesis or based on liver-dependent malfunction tests." Clin Chim Acta. 381:107-113. (2007).
Friedrich-Rust et al. "Comparison of ELF, FibroTest and FibroScan for the non-invasive assessment of liver fibrosis." BMC Gastroentrology 10:103. (2010).
Mamtani et al. "A simple method to combine multiple molecular biomarkers for dichotomous diagnostic classification." BMC Bioinformatics 7:442. (2006).

*Primary Examiner* — Lisa Cook
(74) *Attorney, Agent, or Firm* — Fox Rothschild LLP

(57) ABSTRACT

A method of diagnosing fibrosis in a subject is provided, comprising the steps of: determining a level of PCPE in a body fluid sample obtained from said subject; and detecting an increased level of PCPE in said body fluid sample relative to a normal control level of PCPE, wherein said increased level of PCPE relative to normal control is indicative of fibrosis in said subject. Furthermore, methods for evaluating the pharmacological efficacy of a drug or a drug candidate in treatment of fibrosis in a patient and for monitoring change of fibrosis in a subject are provided.

22 Claims, 21 Drawing Sheets

Fig. 1A

Q15113 Procollagen C-endopeptidase enhancer 1, Homo sapiens (Human)

```
         10         20         30         40         50         60
                                  ↓
....................QTPNY TPPVFLCGGD VKKESGYVAS EGFPNLYPPN 70         80         90        100        110        120
KECIWTITVP EGQTVSLSFR VFDLELHPAC RYDALEVFAG SGTSGQPLGR FCGTFRPAPL 130        140        150        160        170        180
                             ↓            ‡
VAPGNQVTLR MTTDFATSGR GFLLWYSGRA TSTGTEQFCG GRLEKAQGTL TTPNWPESDY 190        200        210        220        230        240
PPGISCSWHI IAPPDQVIAL TFEKFDLEPD TYCRYDSVSV FNGAVSDDSK RLGRFCGDAV 250        260        270        280        290        300
                                  ‡
PGSISSEGNE LLVQFVSDLS VTADGFSASY KTLPRGTAKE GQGPGPKRGT EPKVKLPPKS 310        320        330        340        350        360
                   ‡
QPPEKTEEP SAPDATCPKK QCPRTYTLSS MFGASLNVT ATKSISVREP GEGLAVTVSL 370        380        390        400        410        420
IGAYKTGGLD LPSPPTGASL KFYVPCKQCP PMKKGVSYLL MGQVEEDGP VLPPESFVVL 430        440
                ‡
HRPNQDQILT NLSKPKCPSQ PVPAAASQD        (SEQ. ID NO: 1)
```

↓ CUB1  ‡ CUB2  ‡ NTR
* Signal peptide
* Trypsin peptides
* Potential N-glycosylation site

Fig. 1B

```
Peptides:
     43  GESGYVASEGFPNLYPPNK
     81  VFDLELHPACR
     92  YDALEVFAGSGTSGQR
    131  MTTDEGTGGR
    141  GFLLWYSGR
    150  ATSGTEHQFCGGR
    205  FDLEPDTYCR
    215  YDSVSVFNGAVSDDSR
    215  YDSVSVFNGAVSDDSRR
    300  SQPPEKTEESPSAPDAPTCPK
    306  TEESPSAPDAPTCPK
    325  TGTLQSNFCASSLVVTATVK
    366  TGGLDLPSPPTGASLK
    395  GVSYLLMGQVEENR
    436  KCPSQPVR
```

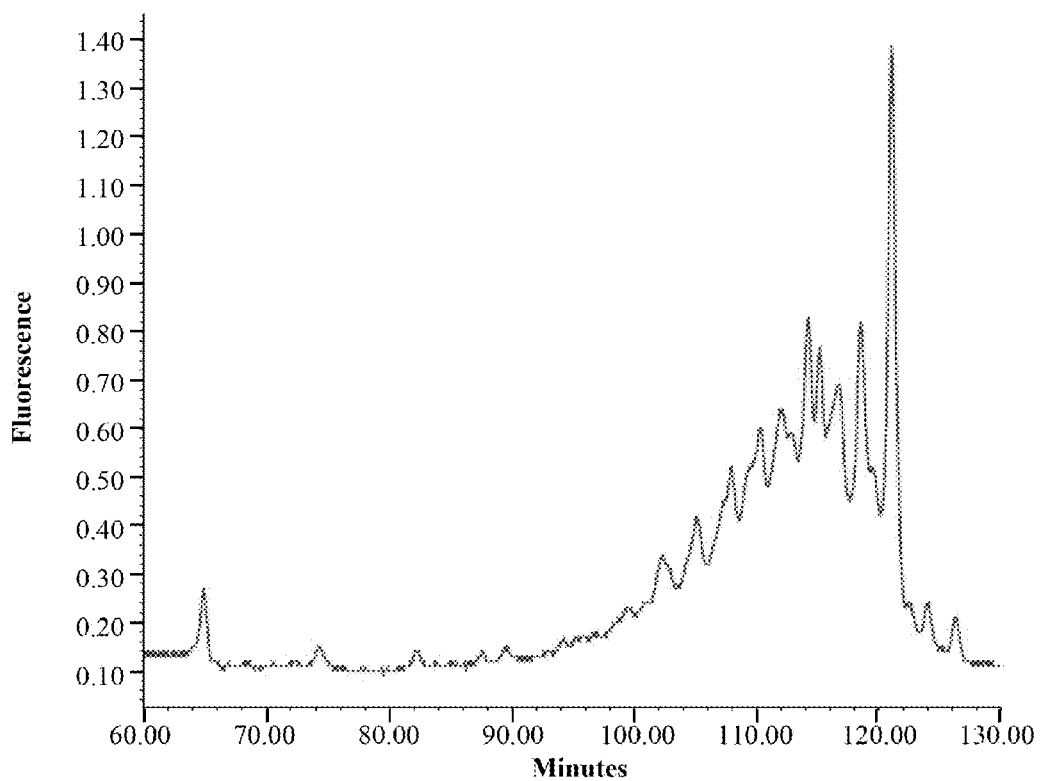

Fig. 13
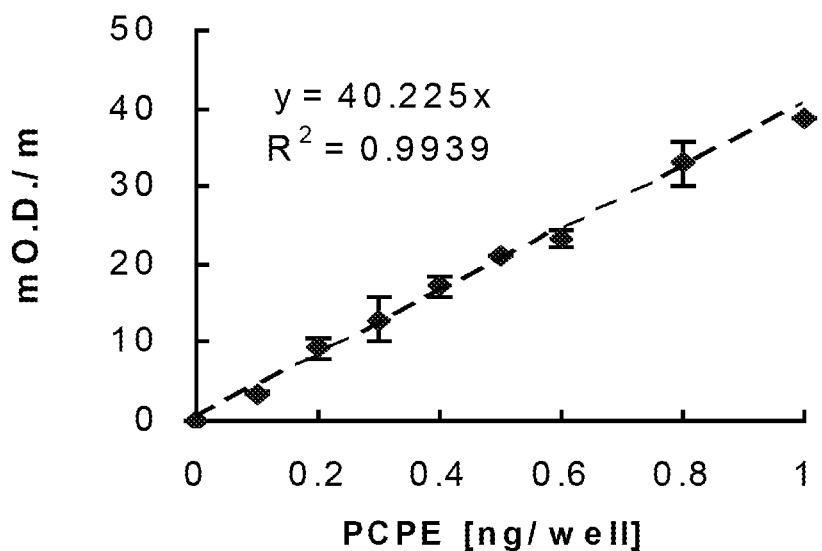
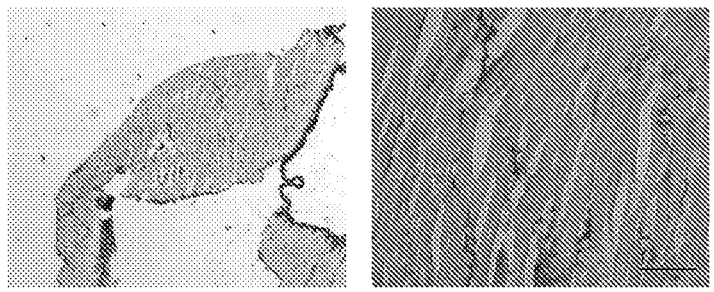
Fig. 14A
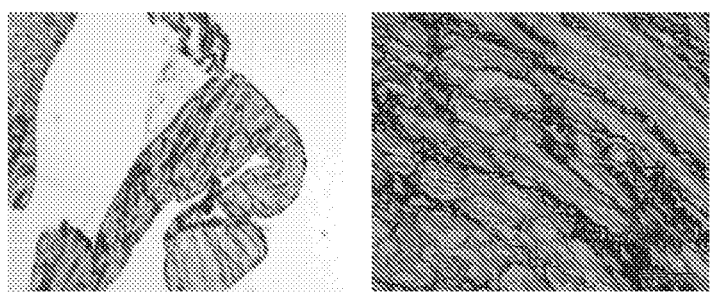
Fig. 14B
Magnification x2   Magnification x20

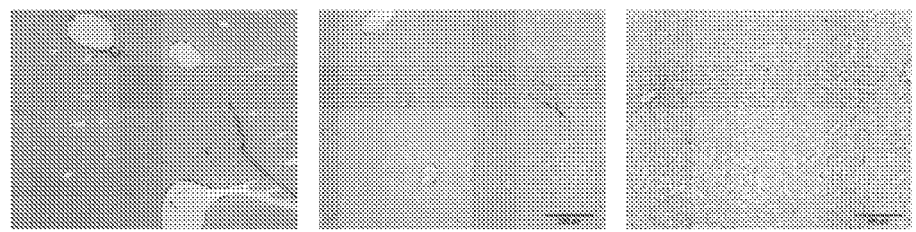
Fig. 17A
Fig. 17B
Magnification x2    Magnification x10    Magnification x20
Fig. 18
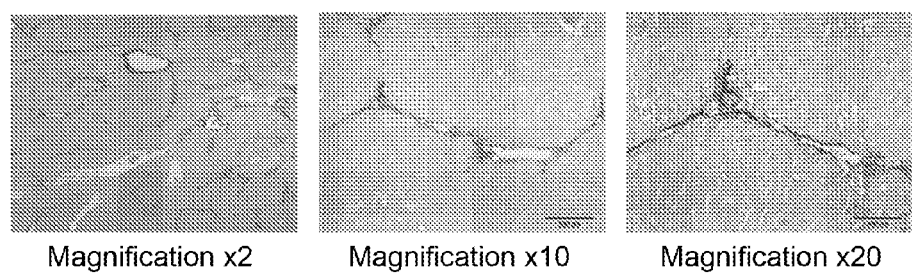
Fig. 19A    Fig. 19B
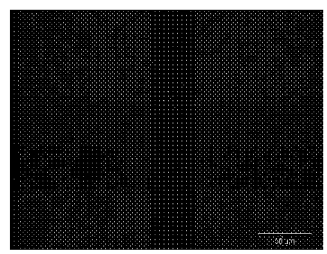 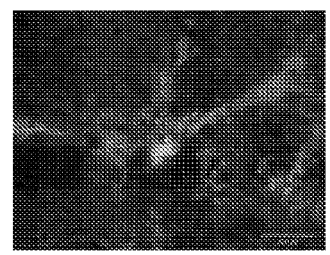

PROCOLLAGEN C-PROTEINASE ENHANCER (PCPE) BIOMARKER FOR BONE FORMATION

This application is a Continuation-in-Part of U.S. application Ser. No. 12/936,035, filed Oct. 1, 2010, which is the U.S. National Stage of International Patent Application Serial Number PCT/IB2009/051376, filed Apr. 1, 2009, which claims priority U.S. Provisional Patent Application No. 61/064,901, filed Apr. 2, 2008. The contents the foregoing applications are hereby incorporated to by reference.

FIELD OF THE INVENTION

The present invention relates to the field of diagnostics, and more particularly, to use of procollagen C-proteinase enhancer (PCPE) as a biomarker for organ fibrosis.

BACKGROUND OF THE INVENTION

Normal bone is constantly being remodeled, or broken down and rebuilt. Every week, humans recycle 5% to 7% of their bone mass. This remodeling process serves two primary functions: maintaining blood calcium levels and keeping the skeleton strong.

Two types of cells are involved in the remodeling of bone: osteoclasts and osteoblasts. Osteoclasts are the cells that break down bone, converting the calcium salts to a soluble form that passes easily into the blood. Osteoblasts produce the organic fibers on which calcium salts are deposited. In healthy young adults, the activities of these two cell types are balanced so that total bone mass remains constant.

Remodeling is a cyclic process that occurs at specific skeletal sites, with each remodeling cycle lasting about four months. Since bone resorption occurs rather quickly, most of the cycle is devoted to bone formation. The major event that triggers bone formation is the transition of mesenchymal stem cells into osteoblast cells. Osteoblasts deposit extracellular matrix (ECM) proteins to form the bone scaffold, which subsequently mineralize[1].

The collagens that form fibrils are the most abundant components of most connective tissue and provide the three-dimensional scaffold that maintains tissue integrity[2-4]. Collagen type I is the major ECM protein of the bone, comprising 90% of its organic mass, and is highly expressed during bone formation[5].

Collagen type I and other filbrillar collagens are first synthesized and secreted into the ECM in the form of soluble precursor, procollagen[6]. Proteolytic processing of procollagen N-propeptide and C-propeptide (PINP and PICP, respectively) by specific N- and C-proteinase lead to the production of mature collagen monomer capable of forming fibrils. PICP is cleaved by bone morphogenetic protein-1 (BMP-1)[7]. BMP-1 is a multi substrate enzyme, among its substrates are procollagen type I, II, III and other ECM precursors, such as lysyl oxidase, laminin 5, chordin, and probiglycan[8,9]. The cleavage of PICP by BMP-1 lowers procollagen solubility by at least a thousand fold and is critical for the self-assembly of collagen fibrils[10]. The rate of this processing appears to control fibril formation[11]. BMP-1 C-propeptide processing activity is regulated by another component of the ECM, PCPE[12, 13].

In their search for bone formation markers, researchers have focused on metabolites and enzymes specific to osteoblast activity, mainly those involved in collagen type I synthesis and mineralization, but each was found to have disadvantages[14, 15].

Current markers of bone formation include, among others, circulating procollagen type I C-propeptide (PICP), osteocalcin (OC), and bone-specific alkaline phosphatase (bone ALP). All of these reflect osteoblast activity during the process of bone formation and can be measured in serum[15].

PICP is a soluble trimeric globular protein, produced simultaneously with the production of mature type I collagen molecules from procollagen, and released into the blood[16]. From the blood it is cleared by liver endothelial cells via the mannose receptor and has a short serum half life of 6-8 min. PICP may arise from other sources like tendons, skin, ligaments, cornea, and many interstitial connective tissues, but these non-skeletal tissues exhibit a slower turnover than bone, and contribute very little to the circulating propeptide pool. Different studies have shown good correlation between serum PICP levels and rate of bone formation but its clinical relevance is still viewed with skepticism[17].

Osteocalcin is the most abundant non-collagenous protein of bone matrix. As opposed to PICP, osteocalcin is exclusively present in bone tissue, increasing significantly when skeletal growth is boosted. However its serum concentration has circadian variations, it is relatively unstable in serum samples and considerable inconsistencies have been reported among laboratories[14]. Other disadvantages include its release during bone resorption and rapid clearance by the kidney. In breast cancer patients with bone metastases, serum OC lacks diagnostic sensitivity compared to bone ALP, but in multiple myeloma patients, low levels of OC were found to be associated with severity of the disease and survival[17].

Bone alkaline phosphatase (bone ALP) is an enzyme localized in the membrane of osteoblasts that is released into the circulation. The liver and the bone isoenzymes are the major contributors to the serum level of total ALP. Serum total ALP activity is the most commonly used marker of bone formation but it lacks specificity. Although most of the methods used to monitor the level of bone ALP have proved to be insensitive, nonspecific (as there was cross-reactivity with liver ALP) or technically complicated, in prostate cancer, bone ALP has been shown to be a more sensitive indicator than total ALP in the detection of bone metastases[17]. The precise function of the enzyme is yet unknown but it obviously plays an important role in osteoid formation and mineralization[15].

U.S. Pat. No. 4,857,456 discloses an assay of BMP and anti-BMP antibody for the diagnosis of bone disorders, which may be carried out by comparing the BMP, anti-BMP antibody, or the ratio of the two to normal assay standards.

US 2003224501 discloses use of BMP polynucleotides, polypeptides, and antibodies for diagnostic use.

U.S. Pat. No. 6,037,139 teaches a system for assaying modulators of procollagen maturation, but does not teach the use of such modulators as biological markers.

U.S. Pat. No. 6,803,453 teaches use of antibodies associated with alterations in bone density. The compositions are useful in the diagnosis, prevention and/or treatment of diseases associated with a loss of bone density, such as osteoporosis.

WO 02/066962 teaches methods for determining cartilage degeneration or regeneration in a joint tissue in a patient by measuring levels of osteogenic protein-1 (OP-1 or BMP7) protein and/or mRNA in synovial fluid or joint tissue.

The background art teaches proteins related to BMP. However, BMP1 is an enzyme, while the remaining BMP proteins are not enzymes and have completely different roles. BMP1 is active post modelling for specific collagen deposition, while the others operate earlier in the process and affect bone cell activities. They are also related to non-bone activities, particularly BMP1. However, none of them are accurate, specific biochemical markers for bone formation which are sufficiently accurate and specific to be used as a single marker.

Bone morphogenetic proteins (BMPs) were first identified in fraction of demineralized bone extracts, and named for their ability to induce ectopic endochondral bone formation when implanted into the soft tissues of rodents[18]. BMP1 differed from the other BMPs members which are all members of the transforming growth factor (TGF)-β superfamily of growth factors, in possessing a distinct protein domain structure, that included a conserved protease domain. To date, at least 20 BMPs have been identified, some of which have been shown in vitro to stimulate the process of stem cell differentiation into osteoblasts in human and animal models. Having realized the osteoinductive properties of BMPs and having identified their genetic sequences, recombinant gene technology has been used to produce BMPs for clinical application—most commonly, as alternatives or adjuncts in the treatment of cases in which fracture healing is compromised. BMP-2 and BMP-7 are approved for clinical use in open fractures of long bones, non-unions and spinal fusion. However, despite significant evidence of their potential benefit to bone repair and regeneration in animal and preclinical studies, there is, to date, a dearth of convincing clinical trials[19].

Fibrosis is a widespread pathological condition characterized by excessive extracellular matrix deposition, with type I collagen (the major fibrillar collagen) being the major component. This process leads to stiffness and loss of function of affected internal organs (e.g., heart, blood vessels, liver, kidney, lungs) and intense scarring of affected skin. Fibrosis can result from acute or chronic stimuli, including infections (viral hepatitis), alcoholism (leading to liver fibrosis/cirrhosis), autoimmune reactions (scleroderma; also known as systemic sclerosis or SSc) and mechanical injury (hypertensive heart disease, myocardial infarction). Nearly 45% of all deaths in the developed world are attributed to some type of chronic fibroproliferative diseases generally described as fibrosis[20]. Quantitation of fibrosis is important in order to assess both the progression of the disease and the therapeutic potential of new treatment protocols as mirrored by the regression of fibrosis. Because fibrosis typically progresses slowly, clinical trials to evaluate new treatment modalities could be long and expensive. Therefore, there is a desperate need to develop non-invasive diagnostic methods of fibrosis, in particular methods relying on a suitable serum marker(s), to quickly quantify changes in the natural history of the disease and assess the severity of the disease[20].

For liver fibrosis, two classes of biomarkers have been identified. Class I markers reflect ECM turnover and fibrogenic cell changes and Class II biomarkers are based on algorithmic evaluation of common functional alterations of the liver that do not necessarily reflect ECM metabolism or fibrogenic cell changes[21,22]

Biomarkers that specifically reflect collagen turnover have been proposed for monitoring both myocardial [reviewed in [23]de Jong et al., 2011 and in [24]López et al, 2010] and liver fibrosis [reviewed in [21]Gressner et al., 2007]. Established serum biomarkers of collagen biosynthesis in cardiac and liver fibrosis are the C-propeptide of type I procollagen (PICP; also used as a marker of bone diseases) and the N-propeptide of type I and type III procollagens (PINP and PIIINP, respectively). Plasma markers of collagen degradation used to follow cardiac fibrosis include the C-terminal telopeptide of collagen type I (ICTP), matrix metalloproteinases (MMPs) 1, 2, 3 and 9, and tissue inhibitors of matrix metalloproteinases (TIMPs)[23]. A serum marker specific to cardiac fibrosis in hypertensive patients is brain natriuretic peptide (BNP)[25]. Together these markers are useful as predictive, prognostic or diagnostic tools.

A commercially available test for liver fibrosis, which is based on the measurement of several Class II biomarkers, called Fibrotest[22], consists of an algorithm of five fibrosis markers, α2-macroglobulin, apolipoprotein A1, haptoglobin, γ-glutamyl transpeptidase (GGT), and bilirubin. Its performance is comparable to that of the ELF-test, which consists of an algorithm of 3 fibrosis markers of ECM metabolism, hyaluronic acid, PIIINP and TIMP-1[22]; Friedrich-rust et al., 2010, hereby incorporated by reference)].

SUMMARY OF THE INVENTION

The background art does not teach or suggest a biochemical marker that provides accurate assessment of bone formation, and is devoid of at least some of the limitations of the prior art.

The present invention overcomes these drawbacks of the background art by providing a method, marker and kit for analysis of bone formation using procollagen C-proteinase enhancer (PCPE), a protein that enhances the synthesis of collagen type I, II and III, as a marker.

The term "PCPE" optionally and preferably refers to a protein that is also known as "Procollagen C-endopeptidase enhancer 1" or "PCPE-1", with SwissProt identifier PCOC1_HUMAN (primary accession number Q15113). The sequence of this protein is given below:

(SEQ ID NO: 1)
MLPAATASLLGPLLTACALLPFAQGQTPNYTRPVFLCGGDVKGESGY

VASEGFPNLYPPNKECIWTITVPEGQTVSLSFRVFDLELHPACRYDALE

VFAGSGTSGQRLGRFCGTFRPAPLVAPGNQVTLRMTTDEGTGGRGFLLW

YSGRATSGTEHQFCGGRLEKAQGTLTTPNWPESDYPPGISCSWHIIAPP

DQVIALTFEKFDLEPDTYCRYDSVSVFNGAVSDDSRRLGKFCGDAVPGS

ISSEGNELLVQFVSDLSVTADGFSASYKTLPRGTAKEGQGPGPKRGTEP

KVKLPPKSQPPEKTEESPSAPDAPTCPKQCRRTGTLQSNFCASSLVVTA

TVKSMVREPGEGLAVTVSLIGAYKTGGLDLPSPPTGASLKFYVPCKQCP

PMKKGVSYLLMGQVEENRGPVLPPESFVVLHRPNQDQILTNLSKRKCPS

QPVRAAASQD.

The data presented herein relate at least primarily to PCPE-1; however other forms of PCPE, such as PCPE-2, are not excluded from being encompassed within the present invention.

According to some embodiments of the present invention, there is provided a use of procollagen C-proteinase enhancer (PCPE), preferably PCPE-1, as a marker of bone formation.

According to other embodiments of the present invention, there is provided a method of analyzing bone formation in a subject, the method comprising: detecting a PCPE pattern in a biological sample from the subject; and comparing the PCPE pattern from the sample of biological fluid with a PCPE pattern of a predetermined standard, wherein PCPE is preferably PCPE-1. The method preferably further comprises separating proteins of the biological sample. Optionally, the separating comprises a technique selected from the group consisting of electrophoresis separation and chromatography separation. Optionally, the electrophoresis separation comprises one or more of SDS-polyacrylamide gel electrophoresis (SDS-PAGE), isoelectrofocusing (IEF) and 2 dimensional electrophoresis (2DE). Optionally, the chromatography separation comprises one or more of gel filtration, adsorption, ion exchange, and affinity separation.

In still another aspect, the present invention provides methods of diagnosing fibrosis in a subject, preferably a human subject/individual, comprising the steps of: determining a level of PCPE in a body fluid obtained from said subject; and detecting an increased level of PCPE in said body fluid relative to a normal control level of PCPE, wherein the increased level is indicative of fibrosis in said subject. Also, methods for evaluating the pharmacological efficacy of a drug or a drug candidate in treatment of fibrosis in a patient and for monitoring change of fibrosis in a subject are provided. Regression of fibrosis in response to anti fibrotic treatment will be reflected in our test by a gradual decrease in PCPE levels up to but not lower than normal control levels.

According to some embodiments, the detecting comprises detecting PCPE with mass spectroscopy, for example LC-MS/MS (liquid chromatography combined with mass spectroscopy for direct detection of the component peptides).

Preferably, the detecting comprises: contacting the biological sample with labeled anti-PCPE antibody to form a PCPE/anti-PCPE antibody complex; and detecting the complex.

Optionally and if anti-PCPE is not labeled, the detecting the complex comprises contacting the anti-PCPE antibody with secondary antibody conjugated to enzyme (ALK, HRP, fluorescence or any other labeling). Also optionally, the detecting the complex comprises visualization by one or more of colorimetric methods and electrochemiluminescence (ECL).

Preferably, the biological sample is selected from the group consisting of serum, plasma, urine, cerebrospinal fluid and cell extract or cell medium.

Optionally, the method is used for one or more of diagnosis of growth disorders, diagnosis of aging, diagnosis of organ fibrosis, diagnosis of osteoporosis, diagnosis of cancer metastasis, and diagnosis one or more of the following diseases: Paget's disease, Osteomalacia, Rickets, bone tumors, osteoporosis, bone changes occurring due to parathyroid disorders and the like. Optionally and preferably, PCPE may be used to diagnose metastasis of cancer cells to bone or out of bone (ie metastasis of a bone related cancer from a primary site in bone tissue to one or more other locations in the body). Non-limiting examples of data from actual patients with breast or prostate cancer demonstrates that PCPE is a useful biomarker that can differentiate between patients with or without bone metastasis or metastases.

According to still other embodiments of the present invention, there is provided a kit for analysis of bone formation, the kit comprising a reagent for purification and detection of PCPE, wherein PCPE preferably comprises PCPE-1. However, without wishing to be limited, the experimental results below relate to PCPE-1 (according to both sequence data from MS and also according to specific binding by an antibody specific to PCPE-1, as described in greater detail below).

Preferably, the reagent comprises an antibody against PCPE. Optionally the kit further comprises an Elisa plate and/or an affinity purification column Optionally, the kit further comprises at least one reagent selected from the group consisting of a buffer, an antibody and a colorimetric reagent.

Optionally, the kit further comprises a western blot substrate and an antibody.

As used herein the phrase "disease" includes any type of pathology and/or damage, including both chronic and acute damage, as well as a progress from acute to chronic damage.

The term "marker" in the context of the present invention refers to a peptide, or a polypeptide, which is differentially present in a sample taken from patients (subjects) having one of the herein-described diseases or conditions, as compared to a comparable sample taken from subjects who do not have one the above-described diseases or conditions.

The phrase "differentially present" refers to differences in the quantity and/or one or more characteristics (such as glycosylation or ubiquination, or other posttranslational modification) of a marker present in a sample taken from patients having one of the herein-described diseases or conditions as compared to a comparable sample taken from patients who do not have one of the herein-described diseases or conditions. The characteristic may optionally also relate to a pattern exhibited by PCPE, for example due to different glycosylation and/or fragmentation of PCPE from a 50 kd protein to two subunits, 30 kd and 20 kd respectively. For example, it is possible a polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of PCPE below.

As another example (and also as shown below), the pattern of PCPE may change, due any change in one or more isoforms, optionally featuring the addition or removal of any particular isoform. Non-limiting examples of such changes include changes to the glycosylation pattern and/or fragmentation pattern and/or some other pattern. The glycosylation pattern may optionally be affected by the amount, number, type and/or location of various saccharides. Any other type of posttranslational modification may also optionally change, including with regard to addition, removal or alteration. There may optionally be changes involving combinations with one or more other proteins or materials, for example with regard to ubiquination, or any other to covalent change to PCPE or a portion thereof.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can be effected by determining a level of PCPE in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, the term "level" refers to the amount of PCPE present. Typically the level of the marker in a biological sample obtained from the subject is different (i.e., increased or decreased) from the level of the same variant in a similar sample obtained from a healthy individual (examples of biological samples are described herein).

Numerous well known tissue or fluid collection methods can be utilized to collect the biological sample from the subject in order to determine the level of PCPE in the subject. Examples include, but are not limited to, blood withdrawal and preparation of serum or plasma from the blood sample, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made. Determining the level of the same variant in normal tissues of the same origin is preferably effected alongside to detect an elevated expression and/or amplification and/or a decreased expression, of the variant as opposed to the normal tissues.

A "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals). A "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

"Detect" refers to identifying the presence, absence or amount of the object to be detected.

A "label" includes any moiety or item detectable by spectroscopic, photo chemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label may be directly or indirectly detectable. Indirect detection can involve the binding of a second label to the first label, directly or indirectly. Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxidase, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture "Immunoassay" is an assay that uses antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide (or other epitope), refers to a binding reaction that is determinative of the presence of the protein in a heterogeneous population of proteins and other biologies. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

Antibodies

"Antibody" refers to a polypeptide ligand that is preferably substantially encoded by an immunoglobulin gene or immunoglobulin genes, or fragments thereof, which specifically binds and recognizes an epitope (e.g., an antigen) with regard to PCPE for example. The recognized immunoglobulin genes include the kappa and lambda light chain constant region genes, the alpha, gamma, delta, epsilon and mu heavy chain constant region genes, and the myriad-immunoglobulin variable region genes. Antibodies exist, e.g., as intact immunoglobulins or as a number of well characterized fragments produced by digestion with various peptidases. This includes, e.g., Fab1 and F(ab)2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The functional fragments of antibodies, such as Fab, F(ab')2, and Fv that are capable of binding to macrophages, are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction;

F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab1 monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. Fv fragments comprise an association of VH and VL chains. This association may be noncovalent, as described in Inbar et al. [Proc. Nat'l Acad. Sci. USA 69:2659-62 (1972O]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Preferably, the antibody of this aspect of the present invention specifically binds at least one epitope of PCPE as described herein. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics. Optionally, a unique epitope may be created in a variant due to a change in one or more post-translational modifications, including but not limited to glycosylation and/or phosphorylation, as described below. Such a change may also cause a new epitope to be created, for example through removal of glycosylation at a particular site. An epitope according to the present invention may also optionally comprise part or all of a unique sequence portion of a variant according to the present invention in combination with at least one other portion of the variant which is not contiguous to the unique sequence portion in the linear polypeptide itself, yet which are able to form an epitope in combination. One or more unique sequence portions may optionally combine with one or more other non-contiguous portions of the variant (including a portion which may have high homology to a portion of the known protein) to form an epitope.

Immunoassays

In another embodiment of the present invention, an immunoassay can be used to qualitatively or quantitatively detect and analyze PCPE as a marker in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker, such as PCPE, can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support. After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

The immunoassay can be used to determine a test amount of a marker (PCPE) in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Preferably used are antibodies which specifically interact with PCPE. Preferred embodiments of antibodies according to the present invention are described in greater detail with regard to the section entitled "Antibodies".

Radioimmunoassay (RIA)

In one version, this method involves precipitation of the desired substrate and in the methods detailed hereinbelow, with a specific antibody and $^{125}$I radiolabeled antibody binding protein (e.g., protein A labeled with radioactive iodine) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme Linked Immunosorbent Assay (ELISA)

This method involves fixation of a sample (e.g., fixed cells or a proteinaceous solution) containing a protein substrate to a surface such as a well of a microtiter plate, either directly or via a first antibody specific for the protein substrate (sandwich ELISA). A substrate specific antibody coupled to an enzyme is applied and allowed to bind to the substrate. Alternatively, a second antibody that is different from the first antibody is applied and this second antibody is then detected with a secondary antibody coupled to an enzyme (sandwich ELISA). Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of color produced is proportional to the amount of substrate present in the sample. A substrate standard is employed to permit quantitation and evaluate accuracy.

Western Blot

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described herein above. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis. Immunochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required.

Fluorescence Activated Cell Sorting (FACS)

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-Imaging Methods

These methods include but are not limited to, positron emission tomography (PET) single photon emission computed tomography (SPECT). Both of these techniques are non-, invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Display Libraries

According to still another aspect of the present invention there is provided a display library comprising a plurality of display vehicles (such as phages, viruses or bacteria) each displaying at least 6, at least 7, at least 8, at least 9, at least 10, 10-15, 12-17, 15-20, 15-30 or 20-50 consecutive amino acids derived from PCPE. Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4): 622-34; Giebel L B et al. "Screening of cyclic peptide phage libraries identifies ligands that bind streptavidin with high affinities" Biochemistry 1995 Nov. 28; 34(47): 15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci U S A 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1E show analysis of human PCPE;

FIG. 13 shows determination of mouse PCPE-1 using an indirect ELISA. Shown is a calibration curve with increasing amounts of purified mouse PCPE-1.

FIGS. 14A-B show Sirius red-stained diaphragm sections from 4 months old mice. (A) C57/B1 mice (control); (B) mdx mice. Sections were examined under a light microscope at 2 and 20 fold magnification as indicated.

FIGS. 17A-B show Sirius red collagen staining of liver sections from control C57/B1 mice (A) and from C57/B1 mice treated with $CCl_4$ to induce fibrosis (B). Animals were killed and their livers removed 4 days after cessation of treatment. Sections were analyzed under light microscope for collagen detection at 2, 10 and 20 fold magnification.

FIG. 18 shows an immunoblot of liver extracts from control and $CCl_4$-treated mice (n=4 in each group). Top, probed with an antibody specific to the C-terminal telopeptide of collagen type I (LF-67); Bottom, probed with an antibody against mouse PCPE-1. The livers were removed 4 days after cessation of a 6 weeks treatment.

FIGS. 19A-B show immunofluorescence analysis of liver sections from control (A) and $CCl_4$ treated (B) mice for the presence of PCPE-1. PCPE-1 was detected using a rabbit polyclonal antibody against mouse PCPE-1 as the primary Ab and a CY2-goat anti rabbit IgG as the secondary Ab. Sections were examined using a regular fluorescence microscope.

DESCRIPTION OF THE PREFERRED EMBODIMENTS

Figure 1E:
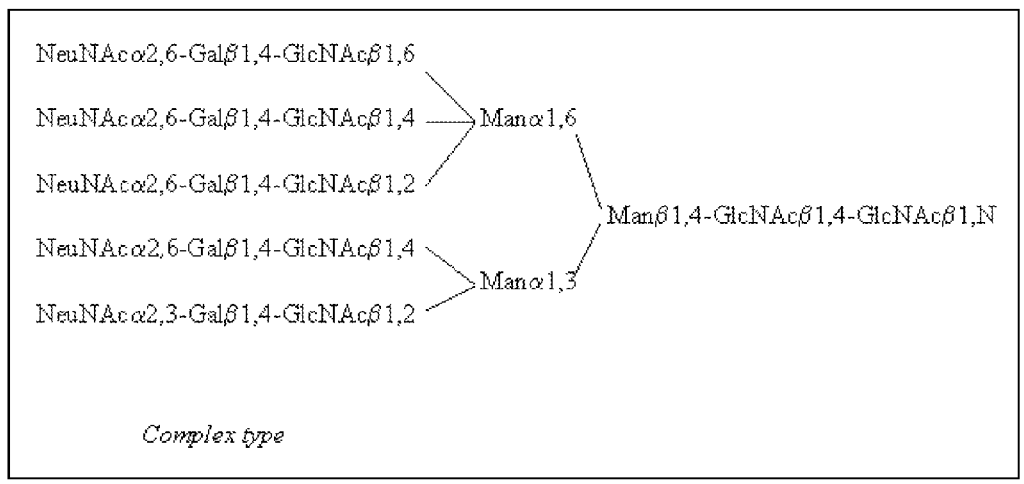

The present invention is of a method for analysis of bone formation using procollagen C-proteinase enhancer (PCPE), a protein that enhances the proteolytic processing and thus, maturation, of collagen type I, II and III, as a marker.

PCPE is a highly conserved ECM glycoprotein devoid of intrinsic enzymatic activity. It binds to the PICP and increases the activity of BMP-1 on procollagen I by up to tenfold[12,13]. PCPE consists of two N-terminal CUB (Complement C1r/C1q, Sea Urchin-EGF or Uegf, and BMP 1) domains, which are essential for its enhancement activity and procollagen binding[20] and a C-terminal netrin-like (NTR) domain, which induces a weak inhibition of matrix metalloproteinase (MMP)[21]. PCPE enhances procollagen type I, II and III C-propeptide processing[22] and binds to mini procollagen type III, processing of which is also enhanced by PCPE[23]. No such enhancement activity was associated with the non fibrillar procollagen substrates of BMP-1. On the basis of these findings Moali[23] suggested that PCPE defines a new class of ECM enzyme adaptors that regulate fibrillar procollagen C-terminal processing activity of BMP-1. PCPE undergoes multiple post-translation modifications as it contains an N-linked oligosaccharide decorated with sialyl residues.[13,21,22]

The present inventors have found that PCPE serves as an accurate, consistent and sensitive marker of bone formation.

The present invention thus provides a method of analyzing bone formation in a subject, using PCPE as a marker. The method comprises obtaining a PCPE pattern, from a biological sample and comparing the pattern to that of a reference sample.

The present invention further provides a kit for analysis of bone formation in a biological sample, comprising reagents for detection of PCPE. The kit may comprise, for example, anti-PCPE antibody (optionally with label and/or conjugated marker and/or any other marker). Optionally, the kit comprises an ELISA plate, PCPE purification column and/or other reagents. Further optionally, the kit may comprise one or more further reagents, such as, for example, buffer, colorimetric reagent and standard sample.

The biological sample for analysis by the method or kit of the present invention may comprise, for example, plasma, serum, urine, cerebrospinal fluid, cell extract, seminal plasma, blood, prostatic fluid, seminal fluid, semen, the external secretions of the skin, respiratory, intestinal, and genitourinary tracts, tears, sputum, saliva, milk, peritoneal fluid, pleural fluid, cyst fluid, broncho alveolar lavage, lavage of the reproductive system and/or lavage of any other part of the body or system in the body. Preferably, the sample is serum.

Optionally and preferably, proteins in the biological sample are separated by one or more techniques selected from the group consisting of electrophoresis (SDS-PAGE, IEF, 2DE), and chromatography (LC-LC, affinity column).

The PCPE pattern is preferably detected by contacting the separated biological sample with anti-PCPE antibody to form a complex of PCPE with the antibody, followed by detection of the complex or direct detection of PCPE protein by representative peptide pattern/profile. Detection may comprise, for example, visualization by colorimetric methods, such as first or secondary antibodies with fluorescence and/or alkaline phosphatase, ECL (by imaging or other methods), or mass spectroscopy (MS) and MS/MS analysis for direct mass detection.

In some embodiments, PCPE is useful as a quantitative biomarker. For quantitative analysis, a plurality of standards are preferably employed to determine a relative concentration curve. The tested concentration of PCPE from the serum of the subject is then compared to the standard concentration curve, in order to determine the relative concentration of PCPE in the serum of the subject. Greater accuracy may optionally and preferably be obtained through the provision of additional standard concentrations for the concentration curve. For example, such a concentration curve with standards may optionally be provided for an ELISA assay.

In some embodiments of the present invention, the type of sugars may optionally be determined, particularly since as described below, PCPE features a plurality of glycosylation sites which show differential sugars depending upon such factors as the age of the subject and so forth. Such differences between different sugars may optionally be obtained by treating PCPE from the serum of a subject with an enzyme or other treatment to alter the sugar content in a specific manner, for example by cleavage of a polysaccharide or portion thereof. The effect of such a treatment on the PCPE may optionally be determined through antibody binding, gel electrophoresis (as removing part or all of the sugars will typically affect the behavior of the protein during electrophoresis, particularly for IEF analysis but also optionally for 1D gels), column chromatography and so forth as is known in the art.

The method or kit of the present invention may be used for detection of disorders that relate to PCPE (i.e. regulation of fibrillar collagen synthesis), particularly bone diseases such as growth disorders (whether genetic or due to malnutrition etc), premature babies, aging, osteoporosis, bone cancer metastasis, and diagnosis of one or more of the following diseases: Paget's disease (excessive resorption of bone by osteoclasts, followed by the replacement of normal marrow by vascular, fibrous connective tissue), Osteomalacia, Rickets, bone tumors, osteoporosis, bone changes occurring due to parathyroid disorders, lymphoma and leukemia typing and in particular the identification of granular lymphocytic leukemia in the bone marrow and Sezary syndrome (an erythrodermic cutaneous T-cell lymphoma with a leukemic component), optionally as well as one or more erosive arthropathy, spondyloarthropathy, lytic bone lesions, and pathologic fractures, whether presenting as the primary disease or sequelae of a different disease process, including but not limited to hemodialysis-related amyloidosis, various diseases featuring renal dysfunction and amyloidosis without hemodialysis. Optionally and preferably, PCPE may be used to diagnose metastasis of cancer cells to bone or out of bone (ie metastasis of a bone related cancer from a primary site in bone tissue to one or more other locations in the body). Normal bone growth may optionally be measured and tracked. The method and kit of the present invention are also useful for detection of organ fibrosis (such as fibrosis of the liver, lung, heart etc), or any other type of fibrosis, whether genetic, cirrhotic (as for alcohol induced hepatic cirrhosis), idiopathic fibrosis, cardiac fibrosis, arterial blockages and/or fibrosis, and so forth.

PCPE may also, in at least some embodiments, be suitable as a clinical biomarker for a drug or other therapeutic treatment. For example, the effect of various treatments on the PCPE pattern in serum from experimental animals is described below. Furthermore, it was shown that the PCPE pattern changes in serum from children having growth problems before and after treatment with growth hormone. The PCPE pattern also changes in cell culture media before and after various treatments, such that PCPE would also be a useful research tool for in vitro experiments.

In other embodiments, PCPE is combined with one or more additional bone markers, such as BMP, alkaline phosphatase and so forth, to provide a more effective diagnostic profile and/or for determining the effect of one or more therapeutic treatments on a subject.

In still other embodiments, PCPE, alone or in combination with one or more other markers, is useful as a marker for determining cell state with regard to differentiation, particularly for osteoblasts and/or fibroblasts. Such a determination may optionally be performed ex vivo, for example for selecting and/or treating cells outside the subject's body, after which optionally the selected and/or treated cells are returned to the subject's body.

The methods and kits of the present invention are further useful in understanding changes in bone physiology that occur during growth, lactation, and menopause, which may optionally be useful for such applications as personalized medicine, tailoring drug regimens, early detection and treatment follow-up, and so forth, early diagnosis and follow-up of fibrillar disorder and diseases.

As discussed in greater detail in the Examples section below, PCPE in serum samples was studied following separation of serum by isoelectric focusing (IEF), SDS-polyacrylamide gel electrophoresis (SDS-PAGE) or two-dimensional electrophoresis (2DE), using IEF and SDS-PAGE combined. Preliminary results suggested that the IEF pattern of human serum PCPE (hsPCPE) may be a bone formation biomarker, however no information exists on the nature of the serum protein. Previous experiments with cell lines show that PCPE is processed into smaller active fragments following its secretion from the cell and undergoes multiple post-translation modifications[28].

Specific detection of PCPE was performed using immunoblotting or immunofixation with commercial PCPE antibodies, followed by silver staining for immunofixation or detection of immunoblot through secondary detection with horseradish peroxidase (HRP)-conjugated antibody and Enhanced ChemiLuminescence (ECL) detection. PCPE in adults, immature and mature babies was studied. A significant difference in the pattern of serum PCPE was detected between immature and mature babies. In adults, another pattern was observed.

As further shown in the Examples section below, changes were seen in the pattern and intensity of serum PCPE in breast cancer patients with bone metastasis.

The inventors of the present invention have previously shown that the expression of PCPE-1 and collagen type I in cultured cardiac cells as well as in the remodeling heart following myocardial infraction is co-regulated[30,31] and that PCPE-1 expression in liver fibrosis is up-regulated in parallel to collagen expression[32].

It has now been found in accordance with the present invention that the level of PCPE in the plasma of mice representing the human diseases of liver fibrosis and muscular dystrophy is substantially elevated when compared to normal control mice. It has further been found in accordance with the present invention that the level of PCPE correlates with the severity of the fibrosis.

Thus, in an additional aspect, the present invention provides methods of diagnosing fibrosis in a subject, preferably a human subject/individual, comprising the steps of: determining a level of PCPE in a body fluid obtained from said subject, and comparing the level of PCPE in said body fluid with a normal control level of PCPE, wherein an increased level of PCPE in said body fluid is indicative of fibrosis in said subject.

The method of diagnosing fibrosis of the present invention is useful for diagnosing fibrosis in an organ selected from the group consisting of liver, lung, heart, kidney, skeletal muscle tissue, or skin.

In a preferred embodiment, the method is used for diagnosing fibrosis in liver, skeletal muscle tissue, or skin.

In certain embodiments, the method of the present invention is useful for diagnosis, follow-up and prognosis of fibrosis caused by or associated with a disease selected from the group consisting of acquired and genetic fibrosis, idiopathic fibrosis, systemic sclerosis (scleroderma), hypertension, cardiac infarction, liver fibrosis, pulmonary fibrosis, renal hypertension, chronic myopathies, muscular dystrophies and scarring, or surgical intervention such as hemodialysis.

Thus, in certain embodiments, the fibrosis in skeletal muscle tissue is caused by or is associated with chronic myopathies or muscular dystrophies, and in other embodiments, the fibrosis in skin is caused by or associated with scleroderma.

The body fluid analyzed in the method of the present invention may be one selected from the group consisting of blood, serum, plasma, and cerebrospinal fluid to (CSF), and is preferably serum or plasma.

As mentioned above, a plethora of methods exist in the prior art for determining the level, i.e. the concentration, of specific molecules in a fluid. In a preferred embodiment, the method used for determining the level of PCPE in the body fluid according to the present invention comprises an immunoassay, such as an ELISA, preferably a sandwich ELISA.

In certain embodiments, the sandwich ELISA of the present invention comprises coating a solid surface, such as a plastic ELISA plate, with a first antibody comprising an anti-human PCPE antibody, such as a mouse monoclonal IgG antibody, and then contacting the anti-human PCPE antibody coated plate with a body fluid that may contain PCPE, or a fragment thereof. In the next step, a second antibody is added, which specifically binds to the bound PCPE if present. The second antibody may be a polyclonal IgG antibody, for example a rabbit polyclonal antibody. However, alternatively, the first antibody may be a polyclonal anti-PCPE IgG antibody and the second antibody may be a monoclonal anti-PCPE IgG antibody. The first and second antibody may be specific to a certain fragment of PCPE, such as any one of its two N-terminal fragments of 34 kDa and 36 kDa, respectively, both of which comprise two N-terminal CUB (Complement C1r/C1q, Sea Urchin-EGF or Uegf, and BMP1) domains, or to the C-terminal netrin-like (NTR) fragment (see Table 1).

The amount of PCPE bound to the first antibody is indirectly determined by adding an enzyme-labeled antibody directed against the second antibody. A chromogenic substrate is added, which is converted by the enzyme to a colored product (chromophore), the concentration of which is measured in a spectrophotometer at a wavelength specific for the product measured. The concentration of the product is, within the linear range of the method, proportional to the level of PCPE in the body fluid sample. Preferably, the PCPE form measured is PCPE-1.

In a preferred embodiment, the increased level of PCPE, which is indicative of fibrosis in a subject, is substantially higher relative to the normal control level of PCPE. In this respect, it has been found in accordance with the present invention that the normal control level of PCPE in serum, i.e. the level of PCPE found in the serum of healthy human individuals, is 324±22 ng/ml. It has further been found in accordance with the present invention that the normal control level of PCPE in plasma, i.e. the level of PCPE found in the plasma of healthy human individuals, is 403±12.8 ng/ml.

The term "normal control level of PCPE" as used herein refers to the normal control level of PCPE in a body fluid unless it is specifically stated, as in for example the term "normal control level of PCPE in a tissue" or "normal control level of PCPE in said tissue".

The term "body fluid" is used herein interchangeably with the term "body fluid sample".

The term "tissue" as used herein refers to solid tissue of the body and does not include body fluids such as blood, serum, plasma, and cerebrospinal fluid.

The absolute normal control level of PCPE as measured in ng/ml can vary depending on the method used to determine the level and according to the sample source. For example, the same method may determine that the level of PCPE in serum is different from the level detected in plasma. The precise cut-off, i.e. normal control level, to be used in diagnosing fibrosis in the clinical settings will be determined according to standard practice on large populations under controlled protocols.

It should be understood that the normal control level of PCPE may vary in different sub-populations, according to for example, gender, age or race. Thus, the normal control level can easily be predetermined for each relevant sub-population according to the method of the present invention, or samples obtained from healthy individuals of the appropriate sub-population may be analyzed as a control in every test performed according to the method of the present invention.

The term "substantially higher level relative to normal control level of PCPE" as used herein refers to a level that is a statistically significant elevated level above the normal control level of PCPE, for example as shown by a Student's t-test, wherein the p-value is below the α-value of 0.05. For example, the average concentration of PCPE-1 in liver fibrosis patients was found herein to be 563±18.7 ng/ml (see Example 17), i.e., a level increased by 39% as compared to control (P<0.0001; calculated using an unpaired, unequal variance, two tailed student's t-test).

Alternatively, the term "substantially higher level relative to normal control level of PCPE" refers in humans to a level of about at least 1, 2, 3, 4, 5, 6, 7, 8, 9, 10, 12, 14, 16, 18 or 20 standard deviation(s) above average normal control levels, i.e., the PCPE level in serum which is indicative of fibrosis in a subject is about at least 350, 375, 400, 425, 450, 475, 500, 525, 550, 575, 625, 675, 725, 775 or 825 ng/ml or higher, and the PCPE level in plasma which is indicative of fibrosis in a subject is about at least 420, 435, 450, 465, 480, 495, 510, 525, 540, 555, 585, 615, 645, 675 or 705 ng/ml or higher, and is preferably about 560 ng/ml.

As a serum marker of collagen biosynthesis, PCPE-1 has the advantage that it functions early in the extracellular maturation pathway of collagen, before the release of the C-propeptide (PICP) from procollagen, so that its serum level may go up before that of PICP. Thus, in certain embodiments, the method of the present invention is useful for the diagnosis of early stages of fibrosis, for example before the appearance of detectable increased levels of PICP in serum or plasma.

In certain embodiments, the method of the present invention further comprises determining the level of additional markers for fibrosis in the body fluid of said subject selected from the group consisting of the N-terminal propeptide of type III procollagen (PIIINP), the C-propeptide of type I procollagen (PICP), the C-terminal telopeptide of type I procollagen, MMPs 1, 2, 3 and 9, TIMP1 (that reflect collagen turn over), FibroTest, i.e. a combination of α2-macroglobulin, apolipoprotein A1, haptoglobin, γ-glutamyl transpeptidase (GGT) and bilirubin, and ELF-test, i.e. a combination of hyaluronic acid, PIIINP and TIMP-1. Thus, algorithms may be used to combine the levels of PCPE and additional markers to improve the specificity and sensitivity of the diagnostic method, as shown for example in Mamtani et al., 2006[33], herein incorporated by reference.

The information regarding the level of PCPE in body fluid samples may be combined with results of PCPE levels in tissue. In one embodiment, the method of the present invention further comprises the steps of: (a) determining a level of PCPE in a sample obtained from a tissue in said subject; and (b) comparing the level of PCPE in said tissue sample with a normal control level of PCPE in said tissue; wherein an increased level of PCPE in said body fluid relative to a normal control level of PCPE in said body fluid, and an increased level of PCPE in said tissue sample relative to a normal control level of PCPE in said tissue, is indicative of fibrosis in said subject.

In certain embodiments, the tissue sample analyzed in the method of the present invention is obtained from a tissue selected from the group consisting of liver, lung, heart, kidney, skeletal muscle and skin. The level of PCPE can be determined in tissue extracts or in growth medium of cells grown in vitro (i.e. determination of secreted to PCPE).

Also, such data can be combined with information of other markers, for instance, CICP (see above), and this may further improve the already accurate method for evaluation of the degree of fibrosis.

In certain embodiments, the method of the present invention further comprises measuring the levels of PCPE in a body fluid sample obtained from a patient at consecutive time intervals. When performed in this way, the method is useful for measuring the efficacy of a treatment of fibrosis, wherein a decrease in the levels of PCPE between measurements is indicative of the efficacy of the treatment.

In an additional aspect, the present invention provides a method for evaluating the pharmacological efficacy of a drug or a drug candidate in treatment of fibrosis in a patient, said method comprising: administering said drug or drug candidate to a patient having fibrosis for a sufficient time period; determining a level of PCPE in body fluid samples obtained from said patient at consecutive time intervals before and after start of administration of said drug or drug candidate; and comparing levels of PCPE in said samples obtained from said patient at consecutive time intervals, wherein a decreasing trend over time towards a normal control level of PCPE is indicative of pharmacological efficacy of said drug or drug candidate in treatment of fibrosis.

The term "sufficient time period" as used herein refers to a time period within which the fibrosis has developed to such an extent that it is recognizable with presently existing diagnostic methods; PCPE can be included as a new marker of fibrosis.

In certain embodiments, said drug or drug candidate is evaluated for its pharmacological efficacy as an anti-fibrotic drug in a disease selected from the group consisting of acquired and genetic fibrosis, idiopathic fibrosis, scleroderma, hypertension, cardiac infarction, liver fibrosis, pulmonary fibrosis, renal hypertension, chronic myopathies, muscular dystrophies and scarring, or surgical intervention such as hemodialysis In yet another aspect, the present invention provides a method for monitoring change of fibrosis in a subject, comprising: determining a level of PCPE in body fluid samples obtained from said patient at consecutive time intervals, and comparing levels of PCPE in said samples obtained from said patient at consecutive time intervals, wherein a decreasing trend over time towards a normal control level of PCPE is indicative of regression of said fibrosis; and wherein an increasing trend over time above a normal control level of PCPE is indicative of progression of said fibrosis.

In still another aspect, the present invention is directed to a kit for methods of diagnosing fibrosis, the kit comprising: an anti-human PCPE antibody for capturing PCPE, or an antibody against a fragment of PCPE, and an ELISA plate, or an ELISA plate coated with anti-human PCPE antibody or antibody against a fragment of PCPE; an anti-human PCPE antibody for detection of bound PCPE, reagents for detecting said antibody; and instructions for use.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods
Serum Collection:

Human blood samples with no additives were collected from 35 adult breast cancer patients (25-80 years of age), with or without bone metastasis, in the oncology unit, or from prostate cancer patients or multiple myeloma cancer patients, all from Chaim Sheba Medical Center, Israel in a tube for blood collection (#367957) BD Vacutainer. Approval for the collection of samples was obtained from the institutional Ethics Committee. Informed consent was obtained from patients before collection. Serum was obtained by centrifugation, 10 min at 1200 g at room temperature (RT). Aliquot samples were stored at −80° C. until analysis. Blood was collected and stored in a similar manner from 12 children: four preterm babies, four term babies and four to older children (age 6-9 years); or from children having growth problems; all at Schneider Children's Medical Center of Israel. Again, approval for the collection of samples was obtained from the institutional Ethics Committee; consent was obtained from parents or guardians as required for under-age minors.

Materials:

Molecular marker-ProSieve colored protein marker was purchased from Cambrex Bioscience.

Non fat dry milk (#170-6404), Tris buffer saline TBSx10, Premixed tris/glycine bufferx10, SDS solution 10% (#161-0416) and Tween 20 (#170-6531) were purchased from Bio-Rad.

Rat Anti human PCPE antibody (# MAB2627 and AF2627 were purchased from R&D Systems, Minneapolis, Minn., USA.

HRP-conjugated Goat anti rat IgG (#3140) and SuperSingel West pico Chemiluminescent substrate (#34077) were purchased from Pierce.

Nitrocellulose (#401381) was purchased from Schleicher & Schuell (S&S). Methanol #1.06009.2500 was purchased from Merck.

PhastGels SDS-PAGE, IEF 3-9, IEF 5-8 (#17-0545-01, 17-0543-01 and 17-0623-01 respectively), PhastGel Buffer strips-SDS (17-0516-01) and Plus One silver stain kit (#17-1150-01) were purchased from Amersham Biosciences.

Tube for blood collection (#367957) BD Vacutainer.

Peptide:N-Glycosidase F (PNGase F) (#P0705S) and Neuraminidase (#0720S) were purchased from New England BioLab.

Lectin binding arrays of Procognia (Israel) Ltd. were used as directed by the manufacturer. More details of these arrays and of their method use are provided in "A lectin array-based methodology for the analysis of protein glycosylation", by Rosenfeld et al, J. Biochem. Biophys. Methods 70 (2007) 415-426, which is hereby incorporated by reference as if fully set forth herein.

Immunoblotting was performed using western blotting as follows. Following gel electrophoresis, the proteins were transferred to nitrocellulose paper with a transfer buffer consisting of 25 mMTris, 129 mMglycine, 20% methanol, and 0.1% SDS. PCPE1 was identified using a specific anti-human PCPE1 antibody (MAB2627; R&D Systems, Minneapolis, Minn., USA). The secondary horseradish peroxidase (HRP)—conjugated antibody (31470; Pierce Biotechnology) was diluted 1:10,000 in to Tris-buffered saline containing 0.05% (v/v) Tween-20. Antigenic expression was visualized by Super Signal West Pico chemiluminescence substrate (34077; Pierce Biotechnology) followed by exposure to X-ray film (Kodak, Rochester, N.Y., USA) according to the instructions of the manufacturer.

Rat and Mouse Experiments—Calorie Restriction

Both rats and mice were subject to an initial phase of calorie restriction of up to 40% reduction in permitted calories. Next, the animals were permitted to eat ad libitum, such that their caloric intake increased above normal to allow the animals to overcome the previous restriction. Serum samples were drawn in a similar manner to that described for human patients above, and PCPE patterns were determined as described herein.

Digestion of Serum Samples with PNGase F and Neuraminidase

A serum sample of 1.5 µl was incubated with 75U PNGase F or 50U neuraminidase (P0705S and P0720S respectively; New England Biolabs, Ipswich, Mass., USA) overnight at room temperature, according to the instructions of the manufacturer.

SDS-Polyacrylamide Gel Electrophoresis (PAGE)

Serum samples (2 µl at 1:30 dilution) were separated in PhastGel homogeneous 12.5% commercial precast gel using PhastGel SDS Buffer strips in PhastSystem (Amersham Biosciences, Piscataway, N.J., USA). The method was performed according to the instructions of the manufacturer.

Two-Dimensional Gel Electrophoresis (2DE)

Serum samples were depleted of albumin and immunoglobulin (depletion kit #89876; Pierce Biotechnology, Rockford, Ill., USA) and loaded onto an Immobiline™ Dry Strip (pH-3-10) (Amersham Biosciences, Piscataway, N.J., USA), on a PROTEAN(R) IEF Cell for the first dimension and a PROTEAN(R) IIXI 2-D Cell (both from Bio-Rad Laboratories, Hercules, Calif.) for the second dimension.

Isoelectric Focusing (IEF)

Serum samples (2 μl at 1:3 dilution) were separated using PhastGel IEF pH 3-9, pH 4.25-6.5 or pH 5-8 commercial precast gels in PhastSystem (Amersham Biosciences). The method was performed according to the instructions of the manufacturer.

Mass Spectroscopy (MS)

MS studies were generally performed as described in "Sample preparation for serum/plasma profiling and biomarker identification by mass spectrometry"; Jose L. Luque-Garcia, Thomas A. Neubert; Journal of Chromatography A, 1153 (2007) 259-276; hereby incorporated by reference as if fully set forth herein.

SaoS-2 and 293T

Cells were maintained in Dulbecco's modified Eagle's medium (DMEM) with 10% fetal bovine serum. Air, 95%; carbon dioxide ($CO_2$), 5% and temperature, 37.0° C.

Recombinant human PCPE produced by NSO cells was bought from R&D Systems Europe (United Kingdom). In all Examples below, reference to "rhPCPE1" or recombinant human PCPE/PCPE1 is to this protein, with the exception of PCPE produced by 293T cells (as described below).

Example 1

Human PCPE Analysis

Purified, isolated recombinant human PCPE1, as well as human serum PCPE1, was analyzed by various methods. The results are shown in FIGS. 1A-E. As shown, FIG. 1A shows LC-MS/MS analysis of recombinant human PCPE1. The analysis covered nearly 60% of PCPE1 amino acid (aa) sequence. Only three regions were not detected by MS analysis. Two of them contain the potential site for N-glycosylation of hPCPE1 (amino acid residues 29 and 431). Glycosylated peptides cannot be identified after MS analysis because the glycan changes the peptide mass and charge. FIG. 1B shows a list of peptides obtained from LC-MS/MS from serum human PCPE1 (shPCPE1) after partial purification on a heparin column; total coverage was 41%. These results are similar to those obtained for fully purified recombinant human PCPE1.

FIG. 1C relates to the presence or absence of various saccharides, which were detected by using the lectin binding arrays of Procognia (Israel) Ltd. as described above, indicating that recombinant human PCPE1 has complex bi-antennary sialylated N-glycans. As described in greater detail below, for diagnostic purposes there may be changes in structure of saccharides and/or in presence or absence thereof. Such changes have been described for other diagnostic proteins (biomarkers), for example in "Altered glycosylation pattern allows the distinction between prostate-specific antigen (PSA) from normal and tumor origins" by Peracaula to et al, Glycobiology vol. 13 no. 6 pp. 457±470, 2003, which is hereby incorporated by reference as if fully set forth herein. In this article, PSA was shown to have a different glycopattern (ie different glycans or saccharides) from prostate tumor cell lines as opposed to PSA obtained in normal seminal fluid. Such differences in the glycopattern of PCPE, including human serum PCPE1, are also encompassed by at least some embodiments of the present invention. Putative or potential glycopattern differences in PCPE1 taken from the sera of patients with a bone or bone related disease, as opposed to normal serum, are described in greater detail below.

FIG. 1D shows the HPLC elution profiles of glycans derived from recombinant human PCPE1 expressed by NSO cells. N-glycans were prepared from purified hPCPE1, derivatized and separated on the positively charged column. The elution retention time of the glycans show that they have extensive amounts of sialic acid. FIG. 1E shows complex-type biantennary N-glycans, of the type which are found on rhPCPE1 as supported by the above results.

Example 2

Human Serum SDS-PAGE Pattern

Serum samples (2 μl at 1:3 dilution) were separated in PhastGel homogeneous 12.5% commercial precast gel using PhastGel SDS Buffer strips in PhastSystem, Amersham Biosciences, and PCPE was detected by immunoblotting with specific anti-PCPE antibody. The method was performed as per the instructions of the manufacturer.

Figure 2:
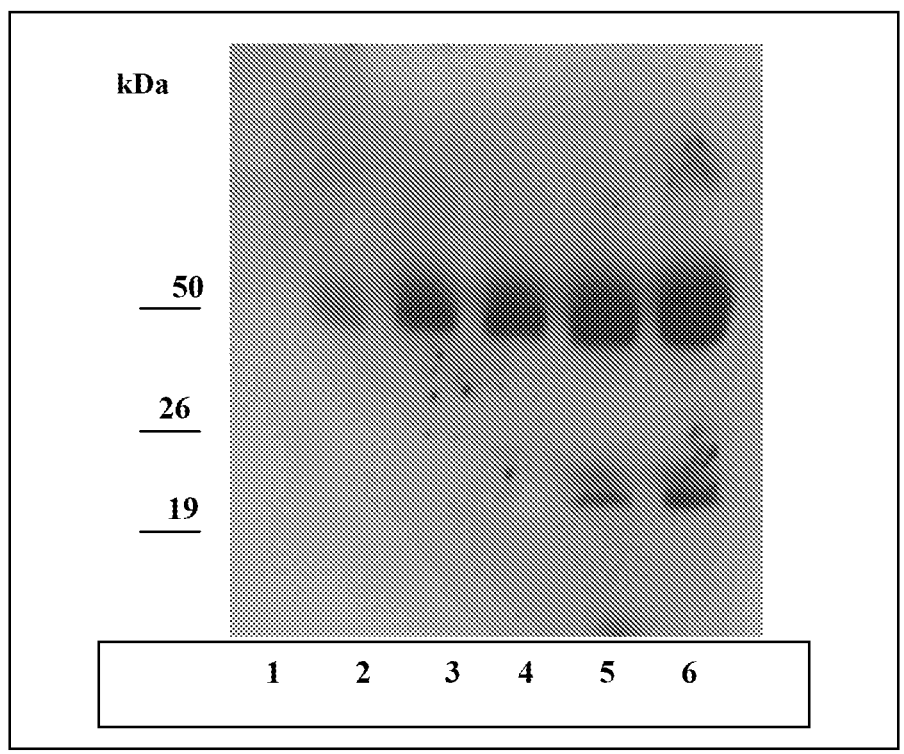
FIG. 2 shows an SDS-PAGE pattern for Human Serum PCPE.

The SDS-PAGE pattern obtained is shown in FIG. 2.

Example 3

Human Serum IEF Pattern

Figure 3:
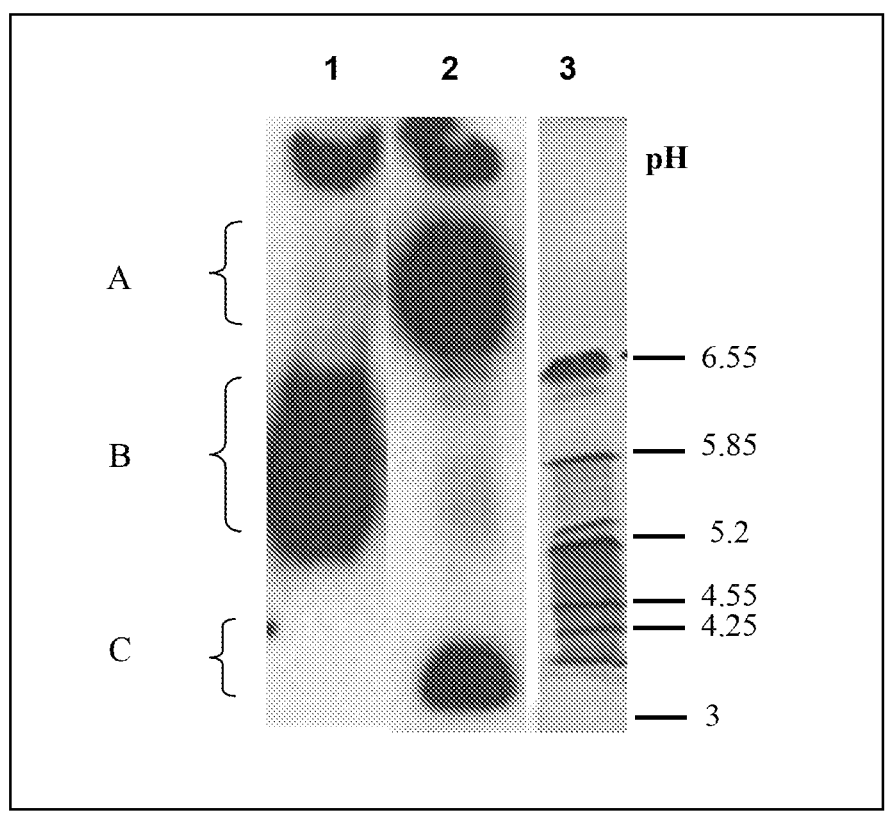
FIG. 3 shows an IEF 3-9 pattern for Human Serum PCPE.

Serum samples (2 μl at 1:3 dilution) were separated in PhastGel IEF 3-9, commercial precast gels in PhastSystem, Amersham Biosciences. PCPE was detected by immunoblotting with specific anti-PCPE antibody. The method was performed as described above for Example 2. Results are shown in FIG. 3.

Example 4

Sensitivity of Human Serum PCPE, IEF Pattern, to Peptide:N-Glycosidase F (PNGase F)

A serum sample 1.5 μl was incubated with 75U of the enzyme PNGase F (lane 2, FIG. 4) or without the enzyme (lane 1, FIG. 4) over night at room temperature according to the enzyme manual. Samples were than separated on IEF gel (pH range 5-8). PCPE was detected by immunofixation with specific antibody. Immunofixation was performed by applying anti-PCPE to the gel after IEF. The interaction of PCPE with its specific antibody results in precipitation of PCPE-antibody complex, which thereby fixes the PCPE to the gel. All other proteins were subsequently washed out of the gel with water, overnight with agitation, and the complexes were detected by protein silver staining (PlusOne silver stain kit Amersham Biosciences)[34].

Figure 4:
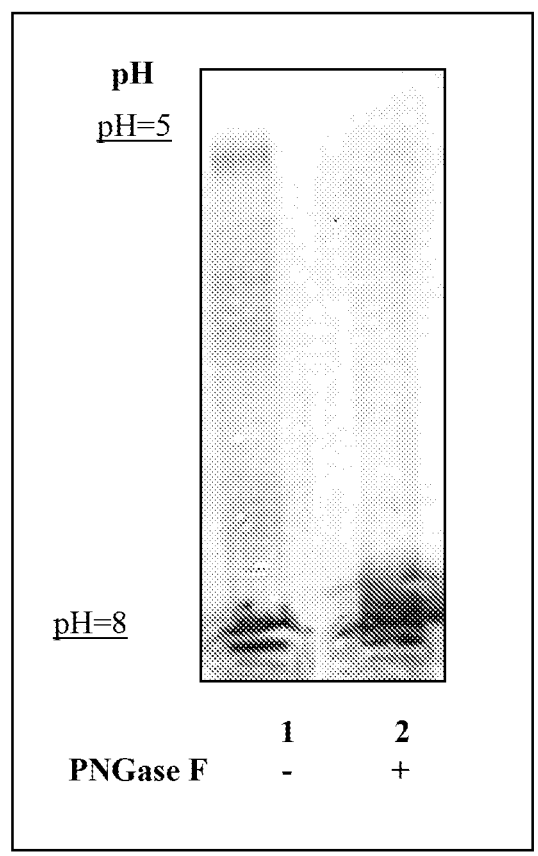
FIG. 4 shows the effect of PNGase F on the IEF pattern of Human Serum PCPE.

The IEF pattern obtained is shown in FIG. 4.

Example 5

Sensitivity of Human Serum PCPE, IEF Pattern, to Neuraminidase

A serum sample 1 μl was incubated with 50U of neuraminidase (lane 1 FIG. 4) or without the enzyme (lane 2 FIG. 5) over night at room temperature according to the enzyme manual. Samples were then separated on IEF gel (pH range 4-6.5). PCPE was detected by immunofixation with specific antibody as described before.

Figure 5:
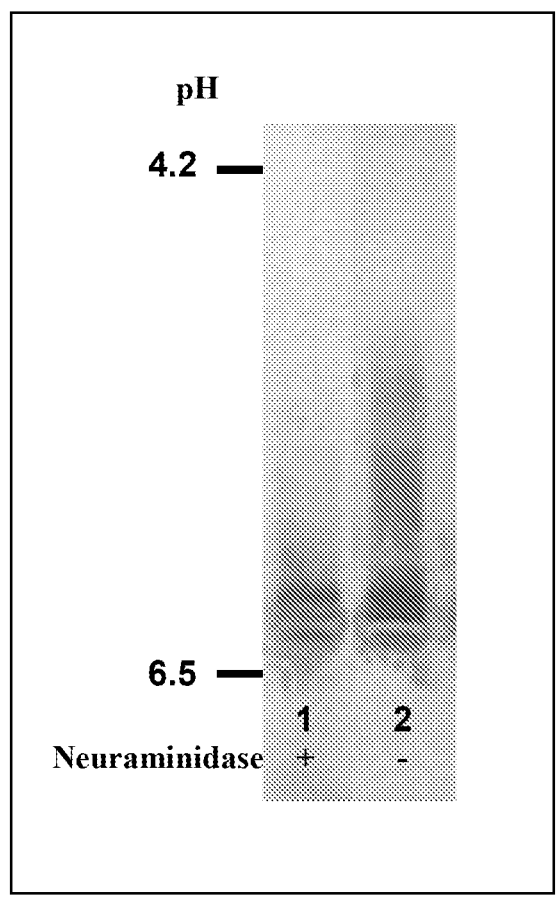
FIG. 5 shows the effect of Neuraminidase on the IEF pattern of Human Serum PCPE.

The IEF pattern obtained is shown in FIG. 5.

Example 6

Human Serum 2 Dimensional Electrophoresis Pattern

Serum sample was depleted from Albumin and Immunoglobulin. The sample was than subjected to 2-dimensional electrophoresis (2DE) using the Immobiline™ Dry Strip (pH-3-10) (Amersham) on a PROTEAN(R)IEF Cell (Bio-Rad) for the first dimension and the PROTEAN(R) IIXI 2-D Cell (Bio-Rad) for the second. Sample was separated on two gels in parallel. Following to the electrophoresis, one gel was subjected to western blot analysis with anti PCPE in order to detect PCPE positive spots (FIG. 6B). The other gel was stained for protein detection with silver stain (FIG. 6A). The spots marked with white circles were analyzed by MALDI T of.

Figure 6:
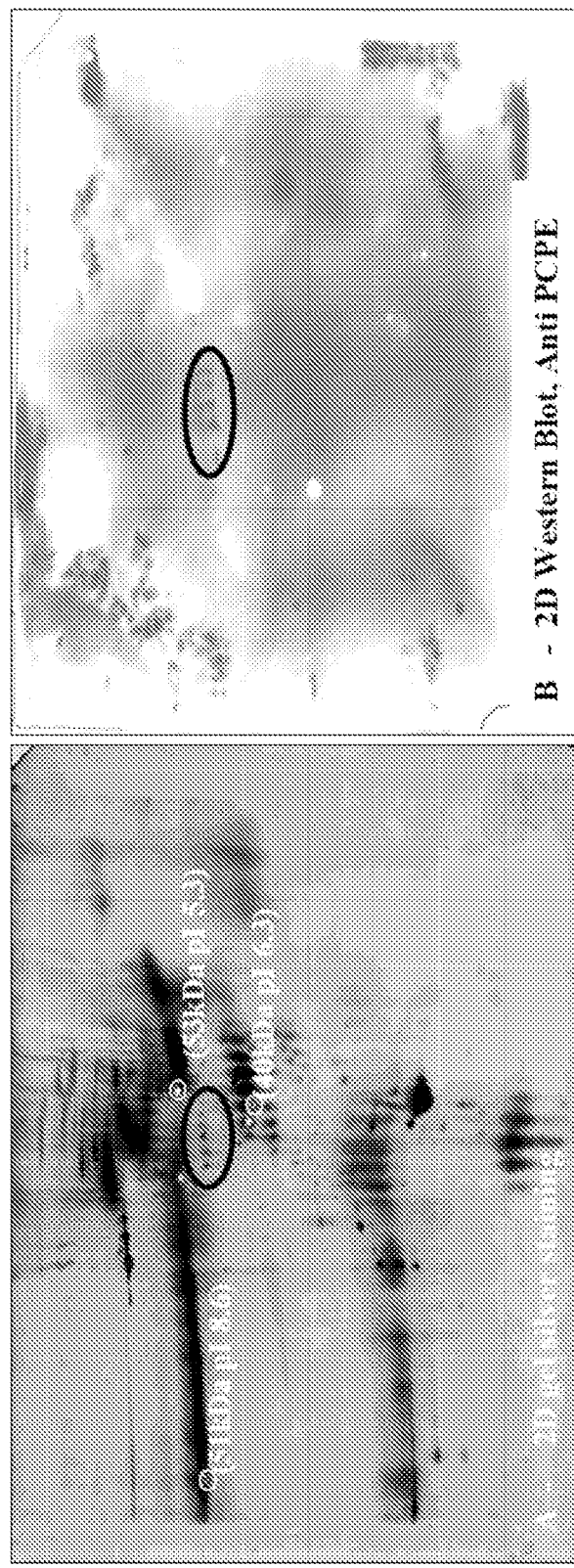
FIG. 6 shows a 2DE pattern for Human Serum PCPE.

The 2DE pattern obtained is shown in FIG. 6.

This technique separates the proteins in two steps according to two independent properties: the first-dimension is isoelectric focusing (IEF) which separates proteins according to their isoelectric points (pI); the second-dimension is SDS-polyacrylamide gel electrophoresis (SDS-PAGE) which separates proteins according to their molecular weights (Mw). Following reduction, alkylation and trypsin digestion, PCPE positive spots from the gel were analyzed by MS/MS in order to get preliminary information about the protein sequences. Part of this work was performed in the protein analyzing department in Tel Aviv University.

Example 7

Growth Dependency of Human Serum PCPE IEF Pattern

Figure 7A:
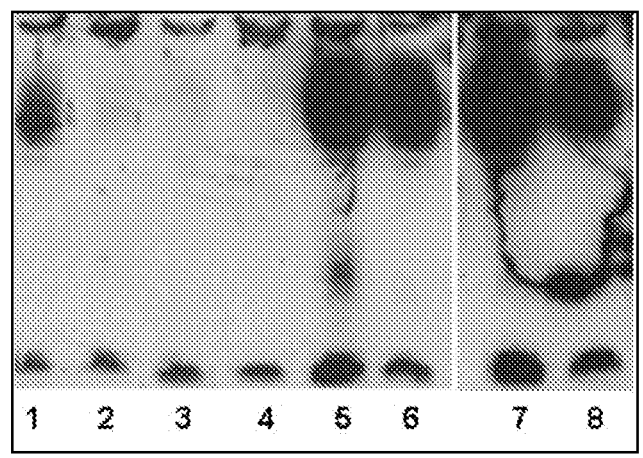
FIGS. 7A-C show IEF patterns for Human Serum PCPE obtained from immature babies and children with growth complication.
Figure 7B:
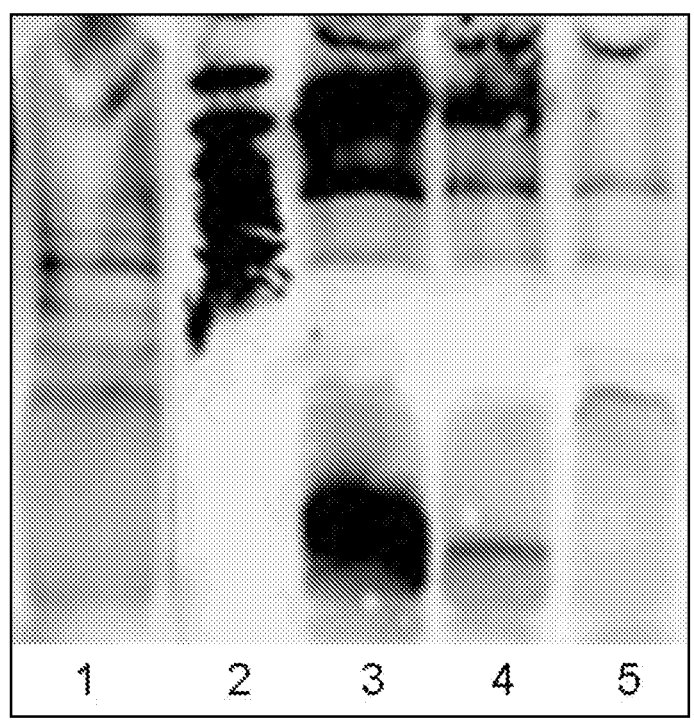

Human serum samples from 4 preterm babies and 4 term babies were separated on IEF gel (pH range 3-9). PCPE was detected by immunoblot with specific antibody for FIG. 7A. The IEF pattern obtained is shown in FIG. 7A. Lanes 1-4 feature serum from preterm infants, while lanes 5-8 feature serum from term infants; PCPE was detected by immunoblot with the previously described specific antibody. FIG. 7B shows the IEF gel with immunoblotting, in which lane 1 shows adult normal serum; lane 2 shows rhPCPE1 and lanes 3-5 show serum from a single significantly premature infant at days 3, 40 and 82 respectively.

Figure 7C:
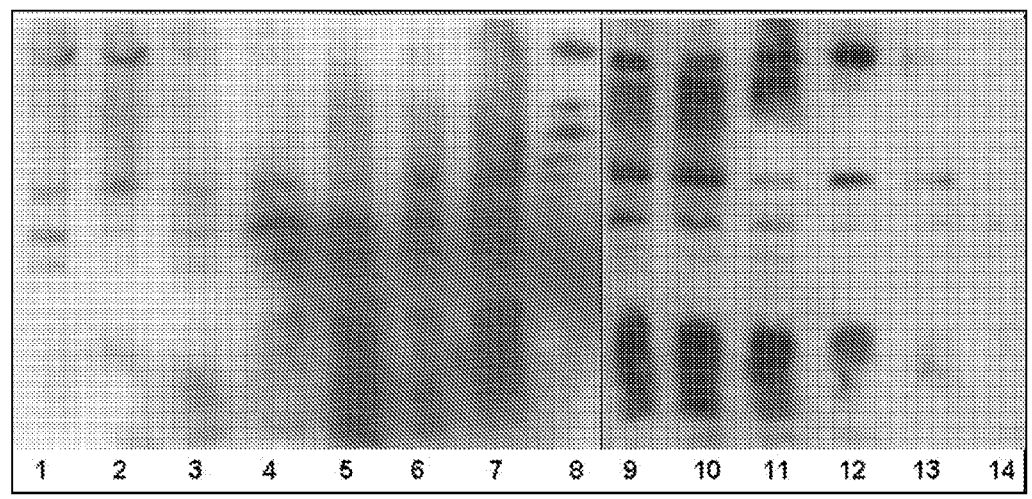

In addition, human serum PCPE patterns were obtained from children treated with GH (growth hormone). Children treated with growth hormone experience additional and/or accelerated growth of body tissues, including of bone tissue. To determine the pattern of PCPE found in human sera taken from such children, human sera samples from such children were subjected to IEF as previously described. Samples were separated on IEF gel (pH range 3-9) as described in Example 3 above. PCPE was detected by immunoblot with specific antibody as previously described. As shown in FIG. 7C, lane 1 shows adult normal serum. Lane 8 shows rhPCPE1. Lanes 2-3; 4-5; 6-7; 9-10; 11-12; 13-14 show the results of serum samples from children diagnosed as suffering from growth problems. Lanes 3, 5, 7, 10, 12, 14 shows serum samples that were taken before GH treatment and 2, 4, 6, 9, 11, 13 show serum samples that were taken three months after GH treatment. Clearly GH treatment causes a change in the PCPE pattern, which may be due to changes glycosylation although it is possible that different changes may be occurring, additionally or alternatively.

Example 8

Correlation of Human Serum PCPE IEF Pattern with Bone Metastasis

Serum samples from breast cancer or prostate cancer patients were separated on IEF gel (pH range 3-9). PCPE was detected by immunoblot with specific antibody.

Figure 8:
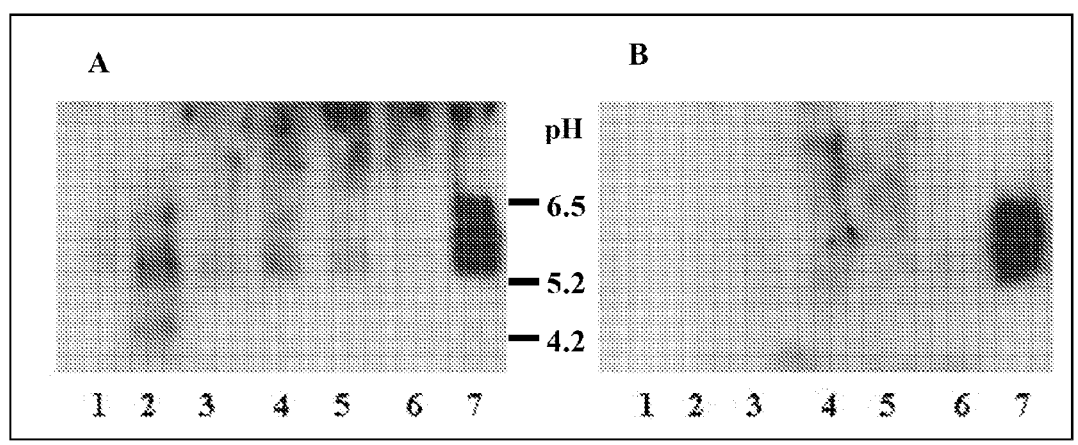
FIGS. 8 and 9 show IEF patterns for Human Serum PCPE obtained from subjects with and without bone metastasis.
Figure 9:
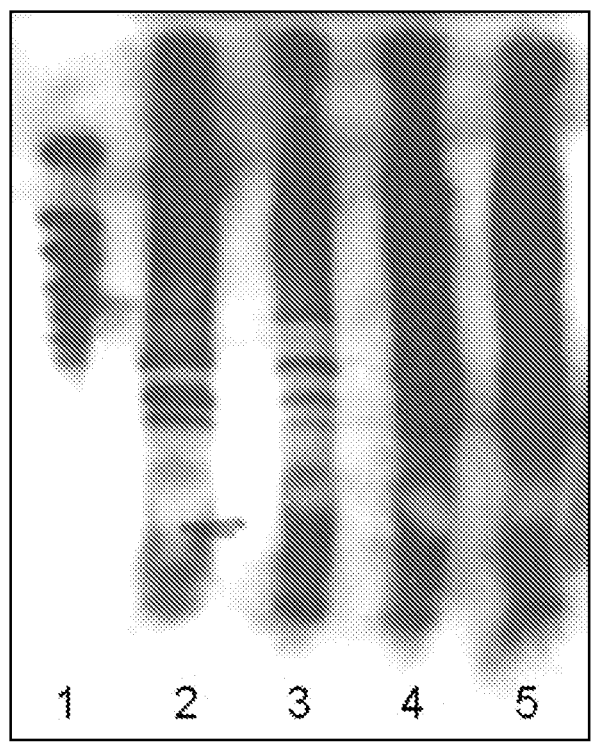

The IEF pattern obtained is shown in FIG. 8 for breast cancer patients and FIG. 9 for prostate cancer patients.

FIG. 8A: Lanes 1-6 show patterns from serum from breast cancer patients with bone metastasis. FIG. 8B: Lanes 1-6 show patterns from serum from breast cancer patients with no metastasis in the bone. FIGS. 8A and 8B: Lane 7 is a positive control for A and B.

FIG. 9: Lane 1 shows recombinant human PCPE1 as a positive control. Lane 2 shows normal serum as a negative control. Lanes 3-5 show serum from patients with prostate cancer, in which serum in lanes 3 and 5 is from patients with bone metastasis and serum in lane 4 is from patients without bone metastasis.

Example 9

Structural Analysis of PCPE

Carbohydrate side chains of glycoprotein play critical roles in numerous biological systems[35]. Therefore information concerning the carbohydrate side chains is of great importance. Towards this purpose, PCPE is purified from serum by immunoaffinity chromatography. The purified protein is analyzed using Tandem Mass Spectrometry (MS/MS) in order to define exact amino acid sequence and to detect glycosylation sites. To elucidate the nature of oligosaccharide chain, the purified protein is digested using endoglycosidases [Endo H, Peptide:N-Glycosidase F (PNGase-F)] and exoglycosidases (Mannosidase, Neuraminidase) and O-glcosydase followed by analysis using the same methods.

Example 10

Osteoblast-Specific Pattern of PCPE

Figure 10:
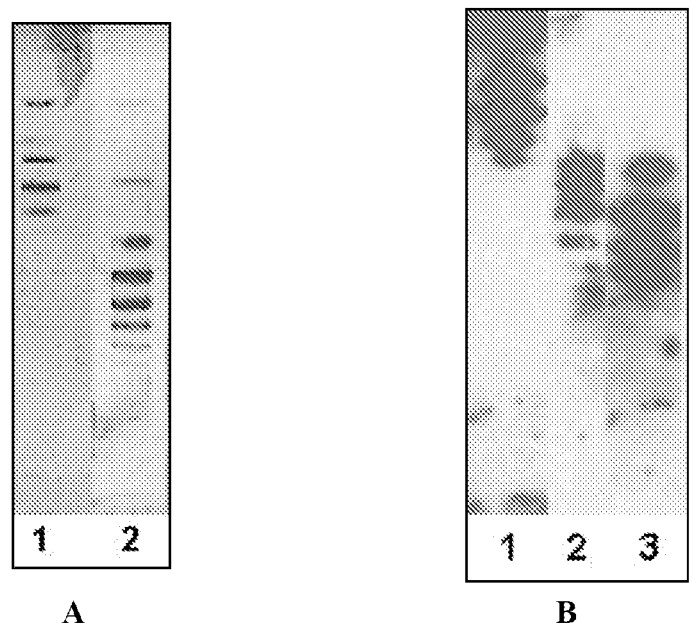
FIGS. 10A-10B show PCPE patterns from different cell lines.

To define an osteoblast specific pattern of PCPE, cell lines were grown, and media was collected from the different cell lines and concentrated with a centricon device. Samples were separated on IEF gel (pH range 3-9) as described in Example 3 above, and the specific cell pattern was analyzed. PCPE was detected by immunoblot with specific antibody as previously described. The results are shown in FIGS. 10A-B. For FIG. 10A, proteins were separated on IEF (pH range 3-9) and detected by silver stain. Lanes 1 and 2 show rhPCPE1 expressed in NSO and 293T cell lines respectively. For FIG. 10B, media was collected from the SaoS-2 cell line. The media was concentrated with a centricon device and separated on IEF gel (pH range 3-9). PCPE was detected by immunoblot with specific antibody as described above. Lane 1 shows rhPCPE from the NSO cell lines. Lane 2 shows hsPCPE1. Lane 3 shows SaoS-2 cell line medium.

The results demonstrate that the serum PCPE is mainly from bone. Furthermore, PCPE from bone cancer samples also has a similar appearance to that of normal bone and hence also serum. However, other cell lines show different results which are presumably due to different glycosylation patterns. Although the concentration may not change, the glycosylation pattern may change between different tissues as shown by these results. Without wishing to be limited by a single hypothesis, it is also possible that the different isoforms (with different glycosylation patterns) show different levels of activity.

Example 11

Human Serum PCPE Patterns Obtained from Multiple Myeloma Patients

Figure 11:
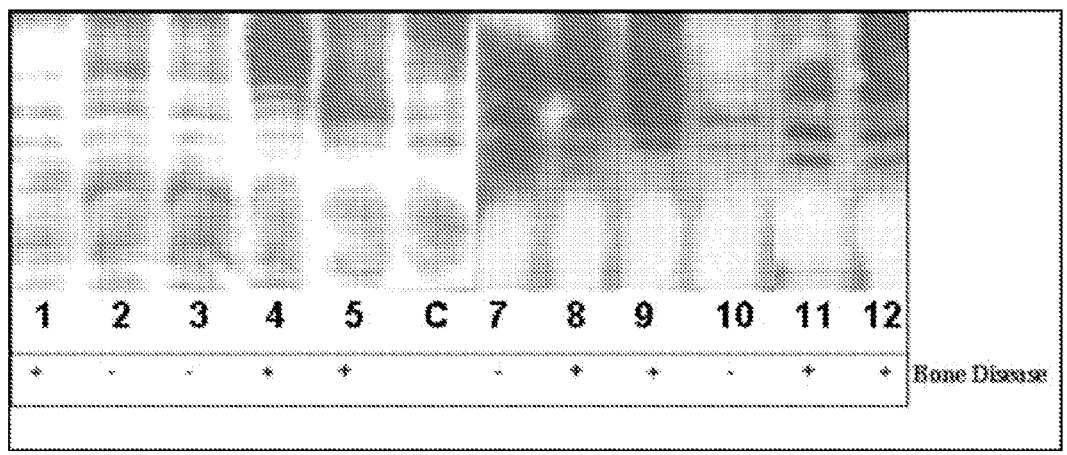
FIG. 11 shows sera from multiple myeloma cancer patients, as compared to sera from patients with other types of bone disease.

Multiple myeloma is a cancer of the bone, and more specifically of the bone marrow. To determine the pattern of PCPE found in human sera taken from such patients (as opposed to patients in which metastasis to bone occurs, in which the primary cancer site is not located in the bone), human sera samples were subjected to IEF as previously described. Samples were separated on IEF gel (pH range 3-9) as described in Example 3 above. PCPE was detected by immunoblot with specific antibody as previously described. As shown in FIG. 11, lanes 1-12 show the PCPE pattern in sera from multiple myeloma cancer patients. Lanes 1, 4, 5, 8, 9, 11 and 12 show sera taken from patients with bone disease, while lanes 2, 3, 7 and 10 show sera taken from patients without bone disease. Lane C shows adult normal serum. As shown by these results, PCPE from multiple myeloma patients shows significant differences in the isoforms for patients suffering from active bone disease as opposed to patients in which bone disease is not active.

Example 12

Human Serum PCPE Patterns Obtained from Adults with Bone Disease

There are various bone diseases which may affect adults, apart from cancer, such as osteoporosis and so forth. To determine the ability of PCPE to act as a biomarker for such diseases, human sera samples from adults with bone disease were subjected to IEF as previously described. Samples were separated on IEF gel (pH range 3-9) as described in Example 3 above. PCPE was detected by immunoblot with specific antibody as previously described. As shown in FIG. 13, lanes 1-6 show serum obtained from patients with a bone disease related to problems of bone metabolism. Lane C shows adult normal serum control, while R relates to to recombinant PCPE. The pattern clearly differs between patients suffering from the bone disease and serum from a normal adult.

Example 13

PCPE Patterns Detected in Non-Human Animals After Various Interventions

It is possible to perform many direct interventions with non-human animals as part of experimental testing which naturally would not be possible with human subjects. Therefore, the effect of various interventions on PCPE patterns in such animals, all from mammalian subjects, was determined. Sera samples from such non-human animals were subjected to IEF as previously described. Samples were separated on IEF gel (pH range 3-9) as described in Example 3 above. PCPE was detected by immunoblot with specific antibody as previously described.

IEF patterns for rat serum PCPE were obtained from animals after treatment, which featured initial calorie restriction, followed by adding back such calories to provide increased food intake. IEF patterns for mouse serum PCPE were also obtained from animals after such treatment, again featuring initial calorie restriction, followed by adding back such calories to provide increased food intake. Briefly, PCPE patterns changed in animals before and after calorie restriction, indicating that specific interventions or treatments cause specific changes in PCPE patterns (data not shown). All experiments involved duplicate animals which displayed similar results. IEF patterns for rat and mouse PCPE were determined in media obtained from mesenchymal stem cells, as well as in osteoblasts, demonstrating that PCPE is secreted by both types of cells (data not shown).

Examples 1-13

Results and Discussion

The results of FIGS. 1A-1E support the determination that recombinant human PCPE1 has complex bi-antennary sialylated N-glycans. Such glycosylation may optionally form an important biomarker, as changes in glycosylation pattern have been shown to be disease related and/or diagnostically specific for other diseases, such as for example PSA glycosylation patterns for prostate cancer and transfferin in congenital disorder of glycosylation (CDG).

As shown in FIG. 2, serum separation on SDS-PAGE gel yielded two bands of hsPCPE, at ~50 kDa and ~22 kDa molecular weight.

PCPE is naturally processed into N-terminal fragments 34 kDa and 36 kDa, both of which also enhance procollagen C-proteinase activity of BMP-1. A 16.5 kDa protein corresponding to a C-terminal fragment of PCPE (known as the netrin (NTR) like fragment) has been described and shown to inhibit matrix metalloproteinase[27]. The band at 50 kDa is probably the holoprotein, and the band at 22 kDa has a molecular weight similar to that of the NTR fragment. No further bands were identified in the serum, which may have occurred because the antibody did not recognize the 30 kDa fragment or that the fragment is missing in the blood.

As shown in FIG. 3, separation of serum samples on IEF gel shows the appearance of multiple bands at three pI zones (zone A at above pH 6.5, zone B at pH 5.2-6.5, and C at pH 3-4.25). The molecular weight, as calculated from the 424 amino acid hPCPE protein deduced from the cDNA sequence is 45.5 kDa (pI 7.55), as seen in Table 1. The actual molecular weight of hsPCPE that is separated on SDS-PAGE is ~50 kDa (FIG. 1), and pI 6.5[36]. It has previously been shown for recombinant human (rhPCPE) that the difference between molecular weight (Mw) calculated by amino acid sequences and the Mw in SDS-PAGE, is due to post translational modifications, N-linked oligosaccharides decorated with sialic acid[28]. As mentioned above, PCPE is naturally processed into fragments 34 kDa-36 kDa, and 16.5 kDa. Theoretically, calculation of the pI's of these fragments, yields pI points 5.5 and 9.44 respectively, as seen in Table 1. The IEF pattern of hsPCPE only partially matches to theoretical pI points, and is more complex.

Complex IEF patterns/profiles are observed for many proteins. Some of the factors that influence the heterogeneity of IEF profiles in glycoproteins are differences in glycosylation, glycation, deamidation, and protein conformation. Among these factors, charge heterogeneity due to variation in glycosylation, in particular sialylation, sulfation, and phosphorylation, plays a major role in determining the IEF behavior of glycoprotein subpopulations.

PCPE contains two potential sites for N-linked glycosylation[26], the first is on amino acid 29 in the first CUB domain (included in the whole protein and 34-36 kDa fragments) and the second is at amino acid 431 in the NTR region (included in the whole protein and the 16.5 kDa fragment). Thus it was assumed that PCPE IEF pattern in the serum is a combination of different molecular weights and different oligosaccharide chains.

Two dimensional electrophoresis (2DE) and tandem mass spectroscopy (MS) were used to define the exact protein sequences of PCPE and its fragments in the serum. Protein sequences of PCPE and its fragments in the human serum were determined, in order to define their glycosylation site and analyze their carbohydrate chains.

Carbohydrate side chains of glycoprotein and posttranslational modification play critical roles in numerous biological systems[35]. Therefore information concerning the carbohydrate side chains is of great importance. To elucidate the nature of oligosaccharide chain the serum protein was digested using endoglycosidase Peptide:N-Glycosidase F (PNGase-F)1 and exoglycosidase Neuraminidase (see Examples 4 and 5 digestion of the serum sample, with PNGase F and Neuraminidase, prior to gel separation, was used to show that the hsPCPE multiple band appearance is due to N-linked glycosylation decorated with sialic acid respectively. PNGase F cleaves between the innermost N-acetylglucosamine (GlcNAc) and asparagine residues of high mannose, hybrid, and complex oligosaccharides from N-linked glycoproteins. Neuraminidase catalyzes the hydrolysis of $\alpha 2$-3, $\alpha 2$-6, and $\alpha 2$-8 linked N-acetyl-neuramic acid residues from glycoproteins and oligosaccharides.

Sensitivity of Human Serum PCPE, IEF pattern, to Peptide:N-Glycosidase F (PNGase F) is shown in FIG. 4. Treatment of serum with PNGase F resulted in disappearance in mobility shifts of PCPE on IEF 5-8 gel (lane 2 FIG. 4), suggesting that hsPCPE has N-linked oligosaccharides.

Sensitivity of Human Serum PCPE, IEF pattern, to Neuraminidase is shown in FIG. 5. Neuraminidase resulted in disappearance in mobility shifts of PCPE on IEF 4-6.5 gel (lane 1), suggesting that hsPCPE N-linked oligosaccharides are decorated with sialyl residues. These results also support the determination of the glycosylation pattern as featuring complex bi-antennary sialylated N-glycans, as determined through MS analysis, column chromatography and lectin array analysis.

Human serum 2 Dimensional Electrophoresis pattern is shown in FIG. 6. As discussed above and shown in FIG. 2, separation of serum sample on IEF gel shows the appearance of multiple bands at three pH zones (zone A—above pH 6.5; zone B—pH 5.2-6.5; and zone C— pH 3-4.25). Separation of adult serum by 2DE as determined by western blot analysis yielded a pattern of 5 positive spots at pH 5.3-6.8 (shown as black circles in FIG. 6B) with molecular weight of ~50-53 kDa (shown as circles in FIG. 6A). Mature babies (lanes 8-11) have strong bands in two pH range zone, A and zone C and faint bands in zone B. Immature babies (lanes 4-7) on the other hand have major bands at pH zone C with faint appearance of bands at zone A. Bone disease of prematurity is a complication of preterm birth[37], hence it seems that PCPE has a unique band appearance in premature infants.

FIGS. 7A and 7B show the different PCPE patterns in preterm babies vs term babies (FIG. 7A), while FIG. 7B relates to multiple samples taken from a premature baby from birth and during a three months' following period that the baby remained in the hospital. The premature baby was born significantly before term, while the preterm babies were only born a few weeks early. In both cases, the PCPE pattern changes in a correlated manner with bone development as the ossification process continues.

As another example of an effect of growth and/or treatments for inducing growth on the PCPE pattern, FIG. 7C shows that growth hormone treatment of children having growth problems causes a change in the PCPE pattern (when comparing sera taken before and after the administration of growth hormone), which may be due to changes glycosylation although it is possible that different changes may be occurring, additionally or alternatively.

As can be seen in FIG. 8A, in serum from breast cancer patients, PCPE bands were mainly identified at zone B (pH 5.2-6.5). IEF separation of serum samples from patient without bone metastasis shows faint or no appearance of PCPE bands (FIG. 8B, lanes 1-6). Similar results are shown in FIG. 9 for prostate cancer patients with or without metastatic bone disease.

It is important to note that all patients with bone metastases are treated with bisphosphonates. Bone metastases are classified as either osteolytic (excessive bone resorption), osteoblastic (excessive bone formation), or mixed, based on their radiographic appearance. However, most blastic metastases have resorptive component, and most lytic lesions are accompanied by some attempt, albeit incomplete, of repair of bone formation[38]. Bone metastases from prostate cancer are predominantly osteoblastic, whereas metastatic lesions in bone from breast cancer can be osteoblastic, osteolytic, or mixed. Thus, high intensity of PCPE band in patient with bone metastases may result from osteoblastic activity in bone.

FIG. 10A shows rhPCPE1 expressed in NSO (mouse myeloma) and 293T (kidney embryonic) cell lines respectively. FIG. 10B compares NSO (mouse myeloma) and SaoS-2 (human bone osteosarcoma) cell lines. These results show that mouse myeloma produces PCPE with different (and presumably defective) sialylation, as compared to recombinant human PCPE1. As noted above, PCPE has a significant amount of sialic acid glycosylation.

FIG. 11 shows that PCPE from multiple myeloma patients has significant differences in the isoforms for patients suffering from active bone disease as opposed to patients in which bone disease is not active.

Figure 12:
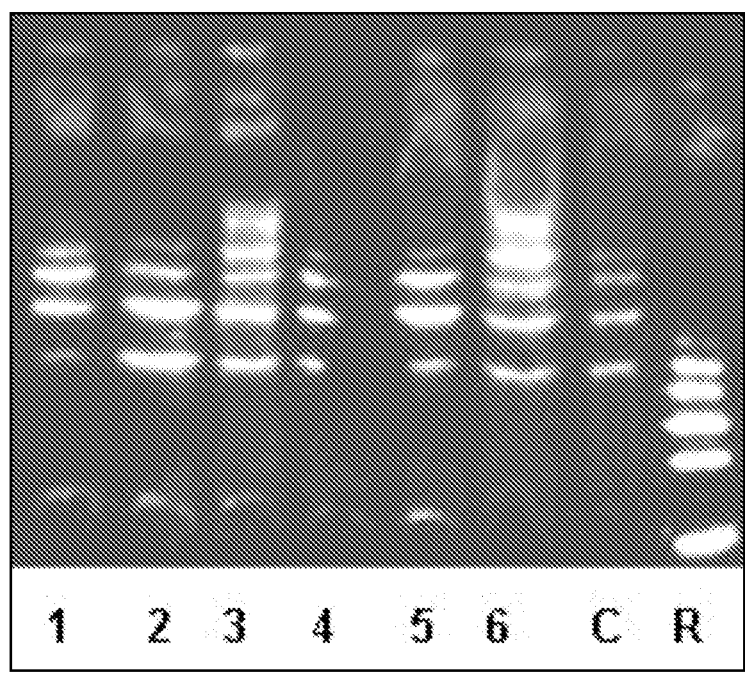
FIG. 12 shows sera from patients suffering from a disease of bone metabolism.

FIG. 12 shows that patients suffering from bone metabolism disease have a different PCPE isoform pattern than the pattern found in normal adult serum.

Further experiments (data not shown) demonstrated that severe caloric restriction of up to 40% in rats and mice, sufficient to significantly reduce growth of the animals, also causes changes in the PCPE isoform pattern, as opposed to animals that were not subject to such caloric restriction. Therefore, PCPE may also be an important diagnostic or prognostic marker for diseases or conditions that affect bone growth. This is also supported by the changes in PCPE patterns seen in children before and after growth hormone treatment, as described above.

All of these results also support the use of PCPE as a clinical biomarker, whether for diagnosis, prognosis, therapy selection or as a clinical endpoint marker (for example for determining the efficacy of a drug in a clinical trial and/or for treating a patient).

Example 14

Development of an ELISA Test for Quantification of Mouse PCPE-1

Mouse PCPE-1 (mPCPE-1) purified from the culture media of 3T6 mouse fibroblasts [[13]Kessler, E., Adar, R.

(1989) Type I procollagen C-proteinase from mouse fibroblasts: purification and demonstration of a 55 kDa enhancer glycoprotein. Eur. J. Biochem. 186:115-121] served as the standard. The method is an indirect (sandwich) ELISA. Wells in a 96 micro well plate are coated with a rat monoclonal Ab (#MAB2239; from R&D Systems, USA) against mouse PCPE-1. mPCPE-1 added to the well is captured by this Ab. Unbound PCPE-1 is washed out and the amount of bound PCPE-1 is then determined using a goat polyclonal Ab against mPCPE-1 (#AF2239, R&D Systems, USA), followed by detection with a secondary, alkaline phosphatase (APA) coupled, antibody (Sigma). APA activity is then determined at 405 nm, using p-nitrophenyl phosphate (pNPP) as the substrate and an ELISA reader.

FIG. 13 shows that a classical linear calibration curve was obtained. The assay is highly sensitive, reproducible and permits quantitation of mPCPE-1 levels in the range 0-1 ng/well (0-20 ng/ml) of mPCPE-1.

Example 15

Fibrosis in Experimental Mice Models is Associated with Increased Plasma Levels of PCPE-1

To examine the potential of PCPE-1 as a plasma/serum marker of fibrosis two experimental mouse models of fibrosis were used: (i) muscular dystrophies x-linked (mdx) mice Mdx mice are deficient in a muscle protein called Dystrophin. As a result, they develop fibrosis of skeletal muscles. Mdx mice are commonly used as a model of fibrosis. Age-matched mice strain C57/B1 served as a control; (ii) $CCl_4$ induced liver fibrosis. In this model, liver fibrosis is induced by repeated administration of $CCl_4$. Liver fibrosis was induced in C57/B1 mice using a standard protocol [Perugorria, M. J., Latasa, M. U., Nicou, A., Cartagena, H., Castillo, J., Goni, S., Zagami, M. G., Loterstajn, S., Prieto, J., Berasain, C., Avila, M. A. (2008). The epidermal growth factor receptor ligand amphiregulin participates in the development of mouse liver fibrosis. Hepatol. 48:1251-1260] by successive intraperitoneal (IP) administration of $CCl_4$ for a period of 6 weeks [Perugorria et al., supra]. Blood samples were removed at appropriate time intervals during the experiment. After killing the animals, the liver was removed for assessment of fibrosis (Sirius red collagen staining, immunofluorescence detection of PCPE-1 and immunoblotting analysis of tissue extracts) to compare PCPE-1 and collagen levels in fibrotic and normal livers.

15.1. Increased Plasma Levels of PCPE-1 in mdx Mice

Before measuring the concentration of PCPE-1 in the plasma, we performed histochemical and immunoblotting analyses to ascertain that the diaphragm of mdx mice (as an example of skeletal muscle) indeed developed fibrosis. Mdx (and control) mice were sacrificed at 4 and 8.5 months of age. Diaphragms were removed, proteins were extracted, and the levels of collagen type I and mPCPE-1 were compared by immunoblotting. Fibrosis (excessive collagen deposition) was also established by Sirius red collagen staining of tissue sections. In addition, blood samples were withdrawn, plasma was prepared and mPCPE-1 level in the plasma samples was determined using the above ELISA assay. In each experiment the ELISA test included a new calibration curve.

FIGS. 14A-B show Sirius-red stained sections of diaphragms removed from mdx and control mice at 4 months. Clearly, sections of diaphragms from mdx mice show high levels of collagen while little or no collagen is detected in sections from control diaphragms. Conclusion: Diaphragms of mdx but not normal mice show high levels of collagen—a characteristic of fibrosis.

Figure 15:
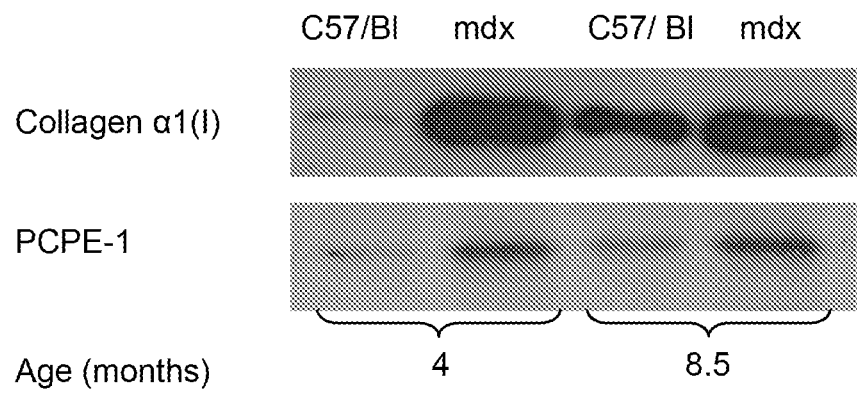
FIG. 15 shows an immublot of protein extracts from diaphragms of mdx and control (C57/B1) mice removed at ages 4 and 8.5 months, as indicated. Top, probed with an antibody to the C-telopeptide of the α1 (I) collagen chain (LF-67); Bottom, probed with a polyclonal rabbit anti mouse PCPE-1 Ab.

Immunoblotting analysis of proteins extracted from the diaphragms of 4 and 8.5 months old mice revealed at least 3 fold increase in the levels of collagen I and PCPE-1 in mdx mice as compared to control at both ages (FIG. 15). Thus, (i) the diaphragm in mdx mice developed fibrosis; (ii) fibrosis (increased collagen expression as also seen in FIG. 14B) is accompanied by increased PCPE-1 expression in the tissue, as we have previously shown using other model systems[30-32].

Conclusion:

Diaphragms of mdx mice show higher levels of collagen type I and PCPE-1 than those of normal controls.

Figure 16:
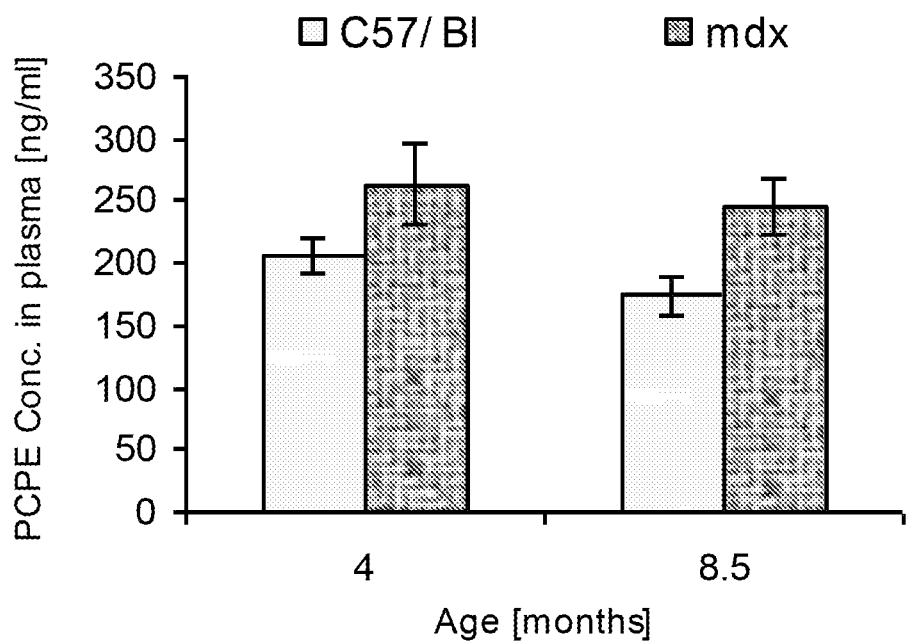
FIG. 16 shows that plasma concentrations of PCPE-1 in mdx mice are higher than in control mice (C57/B1).

To examine whether PCPE-1 levels in the plasma reflect fibrosis, we determined the amounts of PCPE-1 in plasma from control and mdx mice at ages 4 and 8.5 months using the ELISA assay shown in FIG. 13. FIG. 16 shows that at age 4 months, the plasma concentrations of PCPE-1 in the control and mdx mice groups were 206.8±13.8 ng/ml and 262.9±32.6 ng/ml, respectively, namely, the plasma concentration of PCPE-1 in 4 months old mdx mice was 27% higher than that of the control ($p<0.02$, n=8). The average plasma concentrations of PCPE-1 in 8.5 months normal and mdx mice were 174.3±15.5 ng/ml and 244.8±23 ng/ml, respectively. At this age, the plasma concentrations of PCPE-1 were slightly lower than at 4 months. However, the increase rate was higher, reaching 40% ($p<0.02$, n=8).

Mdx Model—Conclusion

The results support the potential clinical value of PCPE-1 as a diagnostic serum marker of fibrosis.

15.2. Increased Plasma Levels of PCPE-1 in Liver Fibrosis

C57/B1 mice were given $CCl_4$ (0.8 µL/gram of body weight; diluted in olive oil) twice a week for up to 6 weeks to induce liver fibrosis. The control group received the same amount of vehicle using the same protocol. In one experiment the animals were sacrificed 4 days after the last injection. In a subsequent experiment, some animals were kept alive for recovery and were sacrificed 2, 4 and 6 weeks after the last $CCl_4$ injection. At each time point, animals were sacrificed, their livers were removed and split into several pieces to be prepared for histochemistry (Sirius red staining), immunofluorescence analysis (PCPE-1) and protein extraction for immunoblotting analysis. Blood was withdrawn once a week or once every other week depending on the stage of the experiment. FIGS. 17A-B show the results of the histochemical analysis for the presence of collagen in liver sections. High amounts of collagen distributed in a typical pattern for liver fibrosis can be seen in the $CCl_4$ treated animals (FIG. 17B) while only background staining is observed in the control (FIG. 17A).

Conclusion:

This result confirms that the liver in the $CCl_4$ treated group developed fibrosis.

Excessive collagen deposition and correlation with PCPE-1 levels were also verified by immunoblotting (collagen and PCPE-1) and immunofluorescence (PCPE-1) analyses. The results (FIG. 18) showed that the livers of the $CCl_4$-treated group contain high levels of both collagen type I and PCPE-1 while only base-line levels of both proteins are detected in the control livers. Increased expression of PCPE-1 in a fibrotic liver (from the $CCl_4$ treated group; FIG. 19B) was also exemplified by immunofluorescence analysis as can be seen in FIGS. 19A-B.

Conclusion:

The results of all three analyses reveal a correlation between PCPE-1 and collagen expression in our mouse model of liver fibrosis, in agreement with our previous studies[30-32].

To examine whether the increased expression of PCPE-1 in liver fibrosis is reflected by elevated PCPE-1 plasma levels, we determined PCPE-1 concentrations in plasma samples from both control and $CCl_4$ treated mice using the ELISA test described in FIG. 13. We analyzed samples from two independent experiments. In both, the same protocol was used for induction of liver fibrosis. However, in the second experiment, some of the animals were left untreated for 3 additional weeks for recovery, to see if PCPE plasma concentrations decline upon healing from this acute condition.

In the first experiment (data not shown), the average PCPE-1 concentration in the control and $CCl_4$-treated groups was 189±11.33 ng/ml and 254±15.38 ng/ml, respectively. Thus, the plasma concentration of PCPE-1 in the $CCl_4$-treated mice increased by ~34% (p<0.02, n=8) as compared to control.

Figure 20A:
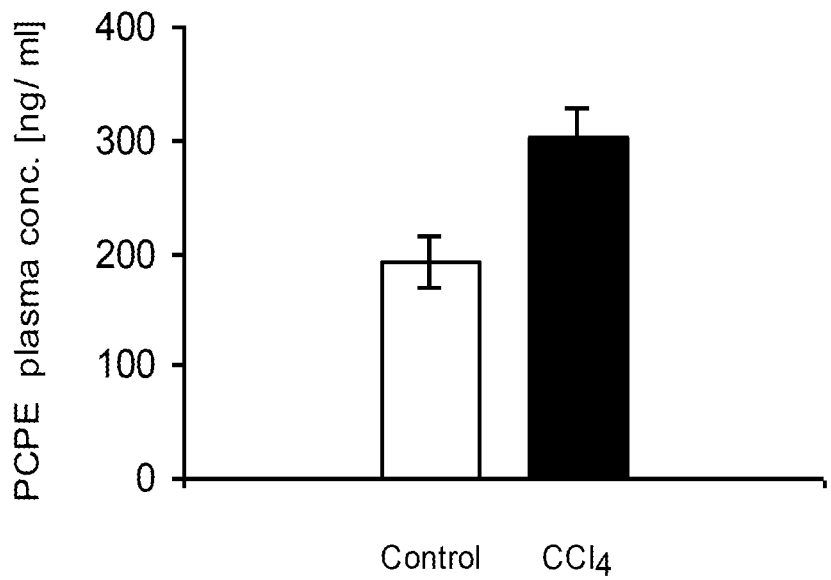
FIGS. 20A-B show that the plasma concentration of PCPE-1 increases in liver fibrosis and reflects the progress of the disease. (A) Average values after 6 weeks of treatment. (B) PCPE-1 plasma concentrations as a function of treatment time. Arrow, time point at which $CCl_4$ treatment was terminated.

In the second experiment, the plasma concentrations of the control group after 6 weeks of treatment remained essentially the same (192±21.16 ng/ml), testifying to the reproducibility and reliability of the assay. The PCPE-1 plasma concentration in the $CCl_4$-treated animals was 302±26.82 ng/ml, namely, it increased by ~57% as compared to control (n=12). (FIG. 20A).

15.3. PCPE-1 Plasma Levels Reflect Severity of Liver Fibrosis

Figure 20B:
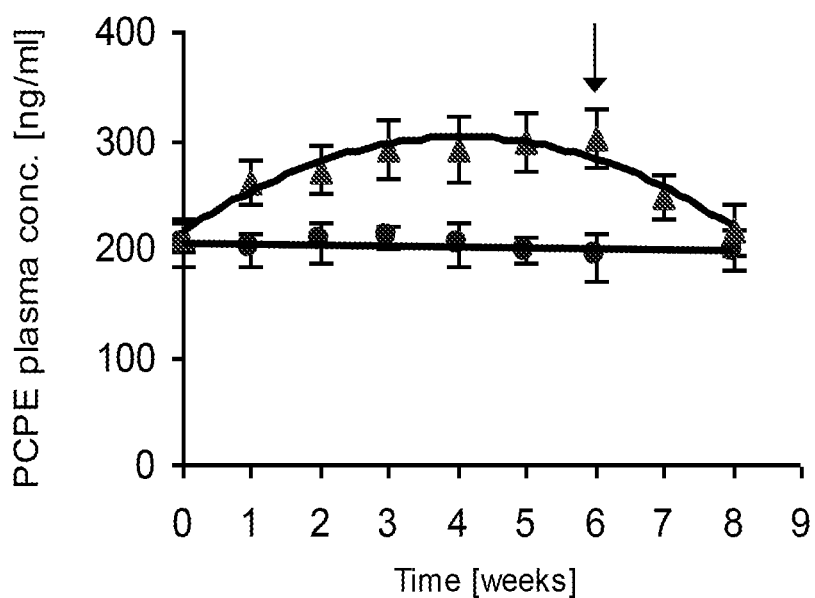

Mice in the second experiment (see 15.2. above) were followed for 4 additional weeks after cessation of treatment. Also, blood samples were removed periodically throughout the experiment in order to examine whether our assay reflects the progress of the disease on one hand and liver recovery after stopping $CCl_4$ administration on the other hand. FIG. 20B shows that this is indeed feasible. PCPE-1 plasma concentration increases gradually during the first 3 weeks of treatment, reaches a maximum between 3-6 weeks, as the treatment goes on, and drops relatively sharply after termination of the treatment, reaching approximately normal levels at 8 weeks, i.e., two weeks after cessation of treatment. In other experiments, it is shown that the level of plasma PCPE parallels the degree of liver fibrosis.

Liver Fibrosis Model—Summary:
In two independent experiments, plasma concentrations of PCPE-1 in liver fibrosis increased 34 to 57% as compared to control;
The increase in PCPE-1 plasma concentration in animals with fibrotic livers appears to reflect the progress and severity of the disease;
The results are highly reproducible, indicating the ELISA assay is reliable;
The results corroborate observations we made using the mdx mice as a model.
Conclusion from both models of fibrosis:
PCPE-1 plasma concentration increases in fibrosis, reflecting the progress of the disease, and decreases in parallel with healing of the fibrotic organ. This strengthens the feasibility of our invention, supporting the clinical potential of PCPE-1 as a new non-invasive marker of fibrosis.

Example 16

An ELISA Test for Determination of PCPE-1 Levels in Human Sera/Plasma 16.1. Development of an ELISA Test for Quantification of Human PCPE-1

Human recombinant PCPE-1 (hPCPE-1) purified from the culture media of HEK-293 cells expressing the protein [29Moali, C., Font, B., Ruggiero, F., Eichenberger, D., Rousselle, P., Francois, V., Oldenberg, A., Bruckner-Tuderman, L., Hulmes, D. J. (2005) Substrate-specific modulation of a multisubstrate proteinase. C-terminal processing of fibrillar procollagens is the only BMP-1 dependent activity to be enhanced by PCPE-1. J. Biol. Chem. 280: 24188-24194.] served as the standard. As in the case of mouse PCPE-1, the method is an indirect (sandwich) ELISA. However in this assay PCPE-1 was captured and detected using PCPE-1 antibodies raised in our laboratory. Wells were coated with a mouse monoclonal Ab (7A11/1; IgG fraction; available from Santa Cruz, Cat #SC-73001, and from Sigma Cat #C2122) and the amount of bound PCPE-1 was determined using a rabbit polyclonal Ab against human PCPE-1 (IgG fraction). Alkaline-phosphatase-coupled goat anti rabbit IgG served as a secondary antibody, facilitating measurement of the rate of increase of absorbance at 405 nm as a result of pNPP hydrolysis by APA as described above for mouse PCPE-1.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference). Briefly, purified PCPE is injected in a rabbit and after an appropriate time period, the rabbit is bled and anti-PCPE antibodies are isolated.

Figure 21:
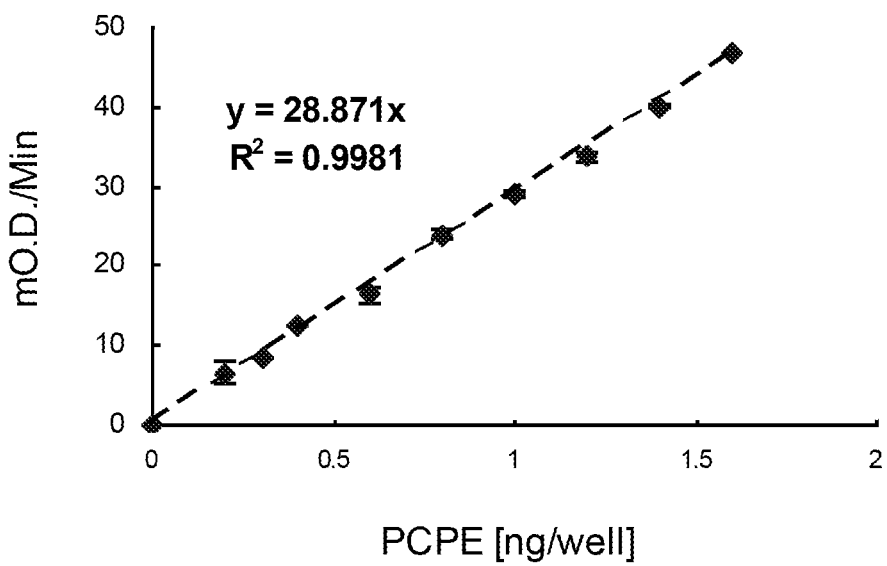
FIG. 21 shows determination of human PCPE-1 using an indirect ELISA. Shown is a calibration curve obtained by adding increasing amounts of purified recombinant human PCPE-1.

FIG. 21 shows that a classical linear calibration curve was obtained. The assay is highly sensitive and reproducible, permitting quantitation of huPCPE-1 levels in the range 0-1.5 ng/well (0-30 ng/ml) of huPCPE-1.

16.2. PCPE-1 Levels in Sera from Normal Human Adults

Using the same assay conditions, we determined the serum concentrations of PCPE-1 in normal human adults (30-50 years old). Serum samples were obtained from the Central Blood Bank of Magen David Adom, Sheba Medical Center. The sera were diluted appropriately and samples of the diluted sera (in triplicates) were analyzed for PCPE-1. We collected data from 11 individuals (6 males and 5 females) and found an average value of 324±21.80 ng/ml of PCPE-1. The values obtained for males and females were essentially the same.

16.3. The ELISA Assay for Human Serum PCPE-1 is Specific

Figure 22:
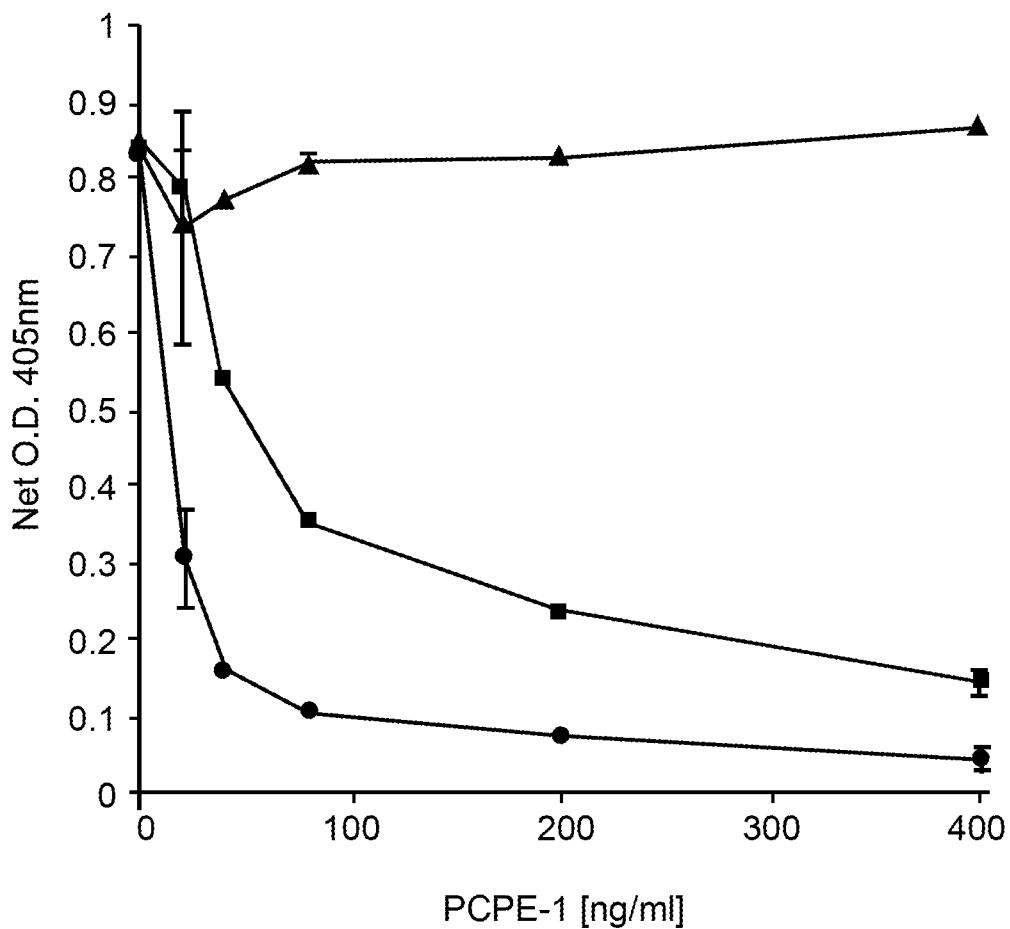
FIG. 22 shows that purified PCPE and human serum but not ovalbumin inhibit binding of Biotin labeled PCPE-1 to the PCPE-1 Ab on the plate. Shown are the results of an ELISA assay in which a constant amount of biotin labeled PCPE-1 was added to the wells in the presence of increasing amounts of unlabeled PCPE-1 (circles), normal human serum (squares) or equivalent amounts of ovalbumin (triangles).

To ascertain the specificity of the assay, we examined whether serum samples can inhibit binding of biotin-labeled PCPE-1 to the PCPE-1 Ab adsorbed to the well. As a positive control (inhibition), biotin-PCPE-1 was mixed with increasing amounts of purified PCPE-1. As a negative control (lack of inhibition), biotin-labeled PCPE-1 was mixed with ovalbumin—an unrelated protein. Binding of biotin-labeled PCPE-1 to the well was measured at 405 nm after incubation with Avidin coupled to alkaline phosphatase. FIG. 22 shows that purified PCPE-1 as well as normal human serum inhibited binding of biotin-PCPE-1 to the well. Ovalbumin at equivalent concentrations had no effect.

Summary—PCPE-1 in Human Serum
We have developed a sensitive sandwich type ELISA for determination of human PCPE-1 concentrations;
The assay is specific and permits determination of PCPE-1 in human sera;
Using this assay we found that the concentration of PCPE-1 in normal human sera is 324±21.80 ng/ml;

Example 17

PCPE-1 in Human Plasma as a Marker for Organ Fibrosis

PCPE-1 was determined as disclosed herein above (Example 16.1) in plasma from human individuals with liver fibrosis.

Plasma samples were obtained from 8 healthy individuals (4 males and 4 females; 28-61 years old) and 3 patients with liver fibrosis (2 males and 1 female), and the plasma levels of PCPE-1 were determined using the ELISA sandwich assay described in example 16.1 above. The average PCPE-1 concentration in the control group, healthy individuals, was 403±12.8 ng/ml. The average concentration of PCPE-1 in liver fibrosis patients was 563±18.7 ng/ml, i.e., it increased by 39% as compared to control (P<0.0001; calculated using an unpaired, unequal variance, two tailed student's t-test).

To be noted, plasma was prepared from blood samples using EDTA as the anti-coagulant. In these conditions, the average PCPE-1 concentration in plasma from normal individuals (403 ng/ml) is higher than that obtained for serum samples (324 ng/ml). Regardless, the results clearly show a substantial increase in the plasma concentration of PCPE in liver fibrosis, providing a proof of feasibility of our invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described with respect to a limited number of embodiments, it will be appreciated that many variations, modifications and other

BIBLIOGRAPHY

01. Gerstenfeld L C, Chipman S D, Kelly C M, Hodgens K J, Lee D D, Landis W J. Collagen expression, ultrastructural assembly, and mineralization in cultures of chicken embryo osteoblasts. J Cell Biol. 1988 106(3):979-89.
02. Myllyharju J, Kivirikko K I. Collagens and collagen-related diseases. Ann Med. 2001; 33(1):7-21.
03. Myllyharju J, Kivirikko K I. Collagens, modifying enzymes and their mutations in humans, flies and worms. Trends Genet. 2004 20(1):33-43.
04. Hulmes D J. Building collagen molecules, fibrils, and suprafibrillar structures. J Struct Biol. 2002 137(1-2):2-10
05. Stein G S, Lian J B, Owen T A. Relationship of cell growth to the regulation of tissue-specific gene expression during osteoblast differentiation. FASEB J. 1990 (13):3111-23.
06. Prockop D J, Kivirikko K I. Collagens: molecular biology, diseases, and potentials for therapy. Annu Rev Biochem. 1995 64:403-34.
07. Kessler E, Takahara K, Biniaminov L, Brusel M, Greenspan D S. Bone morphogenetic protein-1: the type I procollagen C-proteinase. Science. 1996 271(5247):360-2.
08. Prockop D J, Sieron A L, Li S W. Procollagen N-proteinase and procollagen C-proteinase. Two unusual metalloproteinases that are essential for procollagen processing probably have important roles in development and cell signaling. Matrix Biol. 1998 16(7):399-408.
09. Ge G, Greenspan D S. Developmental roles of the BMP1/TLD metalloproteinases. Birth Defects Res C Embryo Today. 2006 78(1):47-68.
10. Kadler K E, Hojima Y, Prockop D J. Assembly of collagen fibrils de novo by cleavage of the type I pC-collagen with procollagen C-proteinase. Assay of critical concentration demonstrates that collagen self-assembly is a classical example of an entropy-driven process. J Biol. Chem. 1987 262(32):15696-701.
11. Kadler K E, Holmes D F, Trotter J A, Chapman J A. Collagen fibril formation. Biochem J. 1996 316 (Pt 1):1-11.

TABLE 1

Summary of human PCPE molecular weight (Mw) and isoelectric points (pI).

|  | Protein | Amino Acid | Potential N-Glycosylation sites (aa) | Predicted from Sequence Mw (kDa) | Predicted from Sequence pI | From Gel Mw (kDa) | From Gel pI |
|---|---|---|---|---|---|---|---|
| Recombinant human PCPE | PCPE | 26-446 | 29, 431 | 45.5 | 7.55 | 55 (Ref 13) | 5.5-6.5 (Lab) |
|  | N-terminal fragment (CUB 1 + 2) | 26-300 | 29 | 29.6 | 5.5 | 34, 36 (Ref 13) | ND |
|  | C-terminal fragment (NTR) | 318-437 | 431 | 12.9 | 9.44 | 16.5 | ND |
| Serum human PCPE | PCPE | 26-446 | 29, 431 | 45.5 | 7.55 | ~51-53 (Lab) | 6.5-7.5 (Lab) |
|  | N-terminal fragment (CUB 1 + 2) | 26-300 | 29 | 29.6 | 5.5 | ND | ND |
|  | C-terminal fragment (NTR) | 318-437 | 431 | 12.9 | 9.44 | ND | ND | rhPCPE = Recombinant human PCPE
shPCPE = Serum human PCPE
ND = Not Detected
Lab = our laboratory results applications of the invention may be made.

12. Adar R, Kessler E, Goldberg B, Evidence for a protein that enhances the activity of type I procollagen C-proteinase. Coll Relat Res. 1986 6(3):267-77
13. Kessler E, Adar R. Type I procollagen C-proteinase from mouse fibroblasts. Purification and demonstration of a 55-kDa enhancer glycoprotein. Eur J. Biochem. 1989 186 (1-2):115-21.
14. Yang L, Grey V. Pediatric reference intervals for bone markers. Clin Biochem. 2006 39(6):561-8.
15. Seibel M J. Biochemical markers of bone turnover: part I: biochemistry and variability. Clin Biochem Rev. 2005 26(4):97-122.
16. Gelse K, Poschl E, Aigner T. Collagens—structure, function, and biosynthesis. Adv Drug Deliv Rev. 2003 55(12):1531-46.
17. Voorzanger-Rousselot N, Garnero P. Biochemical markers in oncology. Part I: molecular basis. Part II: clinical uses. Cancer Treat Rev. 2007 33(3):230-83.
18. Wozney J M, Rosen V, Celeste A J, Mitsock L M, Whitters M J, Kriz R W, Hewick R M, Wang E A. Novel regulators of bone formation: molecular clones and activities. Science. 1988 242(4885):1528-34.
19. Gautschi O P, Frey S P, Zellweger R. Bone morphogenetic proteins in clinical applications. ANZ J. Surg. 2007 77(8): 626
20. Wynn T A. Common and unique mechanisms regulate fibrosis in various fibroproliferative diseases. J Clin Invest. 2007 117:524-529.
21. Gressner O A, Weiskirchen R, Gressner A M. Biomarkers of liver fibrosis: Clinical translation of molecular pathogenesis or based on liver-dependent malfunction tests. Clin Chim Acta. 2007 381:107-113.
22. Friedrich-Rust M, Rosenberg W, Parkes J, Hermann E, Zeuzem S, Sarrazin C. Comparison of ELF, FibroTest and FibroScan for the non-invasive assessment of liver fibrosis. BMC Gastroentrology. 2010 10:103.
23. De Jong S, van Veen T A B, de Bakker J M T, Vos M A, van Rijen H V M. Biomarkers of myocardial fibrosis. J Cardiovasc Pharmacol. 2011 57:373-375.
24. López B, González A, Diez J. Circulating biomarkers of collagen metabolism in cardiac diseases. Circulation 2010 121:1645-1654.
25. Mitchell J A, Ventura H O, Mehra M R. Early recognition and treatment of hypertensive heart disease. Curr Opin Cardiol. 2005 20:282-289.
26. Takahara K, Kessler E, Biniaminov L, Brusel M, Eddy R L, Jani-Sait S, Shows T B, Greenspan D S. Type I procollagen COOH-terminal proteinase enhancer protein: identification, primary structure, and chromosomal localization of the cognate human gene (PCOLCE). J Biol. Chem. 1994 269(42):26280-5.
27. Mott J D, Thomas C L, Rosenbach M T, Takahara K, Greenspan D S, Banda M J. Post-translational proteolytic processing of procollagen C-terminal proteinase enhancer releases a metalloproteinase inhibitor. J Biol. Chem. 2000 275(2):1384-90
28. Steiglitz B M, Keene D R, Greenspan D S. PCOLCE2 encodes a functional procollagen C-proteinase enhancer (PCPE2) that is a collagen-binding protein differing in distribution of expression and post-translational modification from the previously described PCPE1. J Biol. Chem. 2002 277(51):49820-30.
29. Moali C, Font B, Ruggiero F, Eichenberger D, Rousselle P, Francois V, Oldberg A, Bruckner-Tuderman L, Hulmes D J. Substrate-specific modulation of a multisubstrate proteinase. C-terminal processing of fibrillar procollagens is the only BMP-1-dependent activity to be enhanced by PCPE-1. J Biol. Chem. 2005 280(25):24188-94.
30. Shalitin N, Schlesinger H, Levy M J, Kessler E, Kessler-Icekson G. Expression of procollagen C-proteinase enhancer in cultured rat heart fibroblasts: Evidence for co-regulation with type I collagen. J Cell Biochem. 2003 90: 397-407.
31. Kessler-Icekson G, Schlesinger H, Freimann S, Kessler E. Expression of procollagen C-proteinase enhancer-1 in the remodeling rat heart is stimulated by aldosterone. Int J Biochem Cell Biol. 2006 38: 358-365.
32. Ogata I, Auster A S, Matsui A, Greenwell P, Geerts A, D'Amico T, Fujiwara K, Kessler E, Rojkind M. Type I procollagen C-proteinase enhancer protein (PCPE) is expressed in cirrhotic but not in normal rat liver. Hepatology. 1997 26: 611-617.
33. Mamtani Manju R, Tushar P Thakre, Mrunal Y Kalkonde, Manik A Amin, Yogeshwar V Kalkonde, Amit P Amin and Hemant Kulkarni. A simple method to combine multiple molecular biomarkers for dichotomous diagnostic classification. BMC Bioinformatics. 2006 7:442.
34. Dumon M F, Nau A, Hervouet M, Paccalin J, Clerc M. Isoelectric focusing (IEF) and immunofixation for determination of disialotransferrin. Clin Biochem. 1996 29(6):549-53.
35. Varki A. Glycan-based interactions involving vertebrate sialic-acid-recognizing proteins. Nature. 2007 446(7139):1023-9.
36. Pieper R, Gatlin C L, Makusky A J, Russo P S, Schatz C R, Miller S S, Su Q, McGrath A M, Estock M A, Parmar P P, Zhao M, Huang S T, Zhou J, Wang F, Esquer-Blasco R, Anderson N L, Taylor J, Steiner S. The human serum proteome: display of nearly 3700 chromatographically separated protein spots on two-dimensional electrophoresis gels and identification of 325 distinct proteins. Proteomics. 2003 3(7):1345.
37. Sharp M. Bone disease of prematurity. Early Hum Dev. 2007 83(10):653-8.
38. Mundy G R. Metastasis to bone: causes, consequences and therapeutic opportunities. Nat Rev Cancer. 2002 2(8):584-93.

What is claimed is:

1. A method of diagnosing fibrosis in a subject, comprising the steps of:
   a. determining a level of PCPE in a body fluid obtained from said subject; and
   b. comparing the level of PCPE in said body fluid with a normal control level of PCPE,
   wherein an increased level of PCPE in said body fluid relative to a normal control level of PCPE is indicative of fibrosis in said subject.

2. The method of claim 1, wherein said fibrosis is fibrosis in an organ of said subject selected from the group consisting of liver, lung, heart, kidney, skeletal muscle tissue, or skin.

3. The method of claim 2, wherein said fibrosis is caused by or associated with a disease selected from the group consisting of acquired and genetic fibrosis, idiopathic fibrosis, systemic sclerosis (scleroderma), hypertension, cardiac infarction, liver fibrosis, pulmonary fibrosis, renal hypertension, chronic myopathies, muscular dystrophies and scarring, or surgical intervention such as hemodialysis.

4. The method of claim 2, wherein said fibrosis in skeletal muscle tissue is associated with chronic myopathies or muscular dystrophies.

5. The method of claim 2, wherein said fibrosis in skin is associated with scleroderma.

6. The method of claim 1, wherein said body fluid is selected from the group consisting of blood, serum, plasma and cerebrospinal fluid (CSF).

7. The method of claim 1, wherein said subject is a human subject.

8. The method of claim 1, wherein the determining comprises an immunoassay.

9. The method of claim 8, wherein said immunoassay is an ELISA.

10. The method of claim 1, wherein said increased level of PCPE is a substantially higher level of PCPE relative to a normal control level of PCPE.

11. The method of claim 1, for the diagnosis of early stages of fibrosis.

12. The method of claim 1, wherein said PCPE is PCPE-1.

13. The method of claim 1, further comprising determining the level of additional markers for fibrosis in the body fluid of said subject selected from the group consisting of N-terminal propeptide of type III procollagen (PIIINP), the C-terminal propeptide of type I procollagen (CICP), the C-terminal telopeptide of type I procollagen (ICTP), matrix metalloproteinases 1, 2, 3, and 9, TIMP1, a combination of α2-macroglobulin, apolipoprotein A1, haptoglobin, γ-glutamyl transpeptidase (GGT) and bilirubin and a combination of hyaluronic acid, PIIINP and TIMP-1, and brain natriuretic peptide (BNP).

14. The method of claim 1, further comprising the steps of:
   a. determining a level of PCPE in a sample obtained from a tissue in said subject; and
   b. comparing the level of PCPE in said tissue sample with a normal control level of PCPE in said tissue;
   wherein an increased level of PCPE in said body fluid relative to a normal control level of PCPE in said body fluid, and an increased level of PCPE in said tissue sample relative to a normal control level of PCPE in said tissue, is indicative of fibrosis in said subject.

15. The method of claim 14, wherein said tissue is selected from the group consisting of liver, lung, heart, kidney, skeletal muscle and skin.

16. The method of claim 1, further comprising measuring the levels of PCPE in a body fluid sample obtained from a patient at consecutive time intervals.

17. The method of claim 15, wherein said method is conducted as a method for measuring the efficacy of a treatment of fibrosis, wherein a decrease in the levels of PCPE between measurements is indicative of the efficacy of the treatment.

18. The method of claim 15, wherein said method is conducted as a method for monitoring change of fibrosis in a subject, wherein a decrease in the levels of PCPE between measurements is indicative of regression of said fibrosis and wherein an increase in the levels of PCPE between measurements is indicative of progression of said fibrosis.

19. A method for evaluating the pharmacological efficacy of a drug or a drug candidate in treatment of fibrosis in a patient, said method comprising:
   a. administering said drug or drug candidate to a patient having fibrosis for a sufficient time period;
   b. determining a level of PCPE in a body fluid sample obtained from said patient at consecutive time intervals before and after start of administration of said drug or drug candidate; and
   c. comparing levels of PCPE in said samples obtained from said patient at consecutive time intervals,
   wherein a decreasing trend over time towards a normal control level of PCPE is indicative of pharmacological efficacy of said drug or drug candidate in treatment of fibrosis.

20. The method of claim 19, wherein said drug or drug candidate is evaluated for its pharmacological efficacy as an anti-fibrotic drug in a disease selected from the group consisting of acquired and genetic fibrosis, idiopathic fibrosis, scleroderma, hypertension, cardiac infarction, liver fibrosis, pulmonary fibrosis, renal hypertension, chronic myopathies, muscular dystrophies and scarring, or surgical intervention such as hemodialysis.

21. A method for monitoring change of fibrosis in a subject, comprising:
   a. determining a level of PCPE in body fluid samples obtained from said patient at consecutive time intervals; and
   b. comparing levels of PCPE in said samples obtained from said patient at consecutive time intervals,
   wherein a decreasing trend over time towards a normal control level of PCPE is indicative of regression of said fibrosis; and wherein an increasing trend over time above a normal control level of PCPE is indicative of progression of said fibrosis.

22. A kit for methods of diagnosing fibrosis, the kit comprising:

a. a first anti-human PCPE antibody, or an antibody against a fragment of PCPE, for capturing PCPE, and an ELISA plate, or an ELISA plate coated with a first anti-human PCPE antibody or antibody against a fragment of PCPE;
b. a second anti-human PCPE antibody for detection of bound PCPE;
c. reagents for detecting said second antibody; and
d. instructions for use.

* * * * *

SEQUENCE LISTING

<160> NUMBER OF SEQ ID NOS: 1

<210> SEQ ID NO 1
<211> LENGTH: 449
<212> TYPE: PRT
<213> ORGANISM: Homo sapiens

<400> SEQUENCE: 1

```
Met Leu Pro Ala Ala Thr Ala Ser Leu Leu Gly Pro Leu Leu Thr Ala
1               5                   10                  15

Cys Ala Leu Leu Pro Phe Ala Gln Gly Gln Thr Pro Asn Tyr Thr Arg
                20                  25                  30

Pro Val Phe Leu Cys Gly Gly Asp Val Lys Gly Glu Ser Gly Tyr Val
            35                  40                  45

Ala Ser Glu Gly Phe Pro Asn Leu Tyr Pro Pro Asn Lys Glu Cys Ile
        50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125

Leu Arg Met Thr Thr Asp Glu Gly Thr Gly Gly Arg Gly Phe Leu Leu
    130                 135                 140

Trp Tyr Ser Gly Arg Ala Thr Ser Gly Thr Glu His Gln Phe Cys Gly
145                 150                 155                 160

Gly Arg Leu Glu Lys Ala Gln Gly Thr Leu Thr Thr Pro Asn Trp Pro
                165                 170                 175

Glu Ser Asp Tyr Pro Pro Gly Ile Ser Cys Ser Trp His Ile Ile Ala
            180                 185                 190

Pro Pro Asp Gln Val Ile Ala Leu Thr Phe Glu Lys Phe Asp Leu Glu
        195                 200                 205

Pro Asp Thr Tyr Cys Arg Tyr Asp Ser Val Ser Val Phe Asn Gly Ala
    210                 215                 220

Val Ser Asp Asp Ser Arg Arg Leu Gly Lys Phe Cys Gly Asp Ala Val
225                 230                 235                 240

Pro Gly Ser Ile Ser Ser Glu Gly Asn Glu Leu Leu Val Gln Phe Val
                245                 250                 255

Ser Asp Leu Ser Val Thr Ala Asp Gly Phe Ser Ala Ser Tyr Lys Thr
            260                 265                 270

Leu Pro Arg Gly Thr Ala Lys Glu Gly Gln Gly Pro Gly Pro Lys Arg
        275                 280                 285

Gly Thr Glu Pro Lys Val Lys Leu Pro Pro Lys Ser Gln Pro Pro Glu
    290                 295                 300

Lys Thr Glu Glu Ser Pro Ser Ala Pro Asp Ala Pro Thr Cys Pro Lys
305                 310                 315                 320

Gln Cys Arg Arg Thr Gly Thr Leu Gln Ser Asn Phe Cys Ala Ser Ser
                325                 330                 335

Leu Val Val Thr Ala Thr Val Lys Ser Met Val Arg Glu Pro Gly Glu
            340                 345                 350

Gly Leu Ala Val Thr Val Ser Leu Ile Gly Ala Tyr Lys Thr Gly Gly
        355                 360                 365

Leu Asp Leu Pro Ser Pro Thr Gly Ala Ser Leu Lys Phe Tyr Val
    370                 375                 380

Pro Cys Lys Gln Cys Pro Pro Met Lys Lys Gly Val Ser Tyr Leu Leu
385                 390                 395                 400

Met Gly Gln Val Glu Glu Asn Arg Gly Pro Val Leu Pro Pro Glu Ser
                405                 410                 415
```

```
Phe Val Val Leu His Arg Pro Asn Gln Asp Gln Ile Leu Thr Asn Leu
            420                 425                 430

Ser Lys Arg Lys Cys Pro Ser Gln Pro Val Arg Ala Ala Ala Ser Gln
            435                 440                 445

Asp
```